US006265229B1

(12) United States Patent
Fodstad et al.

(10) Patent No.: US 6,265,229 B1
(45) Date of Patent: *Jul. 24, 2001

(54) METHOD AND DEVICE FOR DETECTION OF SPECIFIC TARGET CELLS IN SPECIALIZED OR MIXED CELL POPULATIONS AND SOLUTIONS CONTAINING MIXED CELL POPULATIONS

(75) Inventors: Øystein Fodstad, Oslo; Hanne Kleppe Høifødt, Hvalstad; Philip Rye, Oslo, all of (NO)

(73) Assignee: Oystein Fodstad, Oslo (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/704,619

(22) PCT Filed: Mar. 10, 1995

(86) PCT No.: PCT/NO95/00052

§ 371 Date: Nov. 4, 1996

§ 102(e) Date: Nov. 4, 1996

(87) PCT Pub. No.: WO95/24648

PCT Pub. Date: Sep. 14, 1995

(30) Foreign Application Priority Data

Mar. 10, 1994 (NO) ........................................ 940866

(51) Int. Cl.[7] .......................... G01N 33/553; B01L 11/00

(52) U.S. Cl. .......................... 436/526; 422/101; 435/7.2; 435/7.21; 435/7.23; 435/7.24; 435/33; 435/395; 436/518; 436/525; 436/526; 436/809

(58) Field of Search .............................. 422/101; 435/7.1, 435/7.2–7.32, 29, 30, 33, 383, 395, 401, 975; 436/518, 525, 526, 808, 809

(56) References Cited

U.S. PATENT DOCUMENTS 4,219,411  8/1980  Yen et al. .

(List continued on next page.)

FOREIGN PATENT DOCUMENTS 3811566  10/1988  (DE) .

(List continued on next page.)

OTHER PUBLICATIONS

Bennick et al., "A Rapid Method for Selecting Specific Hybridoma Clones using Paramagnetic Dynabeads," Scand. J. Immunol. 38:212–214, 1993.*

(List continued on next page.)

*Primary Examiner*—Long V. Le
*Assistant Examiner*—Gailene R. Gabel
(74) *Attorney, Agent, or Firm*—Merchant & Gould P.C.

(57) ABSTRACT

The invention relates to a method and apparatus for detecting specific target cells in a simple and time-saving way, using paramagnetic particles, antibodies recognizing the Fc portions of target-cell associating antibodies and target-cell associating antibodies directed to specific antigen determinants in the target-cell membranes. Incubation of the cell suspension with detergent and/or second antibodies or antibody fragments, prelabeled or not with fluorescent agents, metallocolloids, radioisotopes, biotin complexes or certain enzymes allowing visualization, dramatically increase the specificity of the method. The method and apparatus described provides a solid support and permanent record which is easily viewed by microscopy, permits viewing and quantification of the whole specimen rather than small fractions thereof and allows the use of large specimen volumes to be analysed, the device may also be scanned automatically by conventional densitometric technology. The method and apparatus can be used for isolation of the target cells by magnetic field application, and a kit and apparatus for performing the method according to the invention is described.

88 Claims, 5 Drawing Sheets

U.S. PATENT DOCUMENTS

| | | |
|---|---|---|
| 4,510,244 | 4/1985 | Parks et al. . |
| 4,659,678 | 4/1987 | Forrest et al. . |
| 4,710,472 | 12/1987 | Saur et al. . |
| 4,752,569 | 6/1988 | Terasaki et al. . |
| 4,857,452 | 8/1989 | Ho . |
| 4,920,061 | 4/1990 | Poynton et al. . |
| 4,925,922 | 5/1990 | Byers et al. . |
| 5,019,497 | 5/1991 | Olsson . |
| 5,095,097 * | 3/1992 | Hermentin et al. ............... 530/391.5 |
| 5,194,300 | 3/1993 | Cheung . |
| 5,219,763 | 6/1993 | Van Hoegaerden . |
| 5,256,532 * | 10/1993 | Melnicoff et al. ........................ 435/5 |
| 5,264,344 * | 11/1993 | Sneath ................................ 435/7.32 |
| 5,290,707 | 3/1994 | Wood . |
| 5,322,678 | 6/1994 | Morgan, Jr. et al. . |
| 5,326,696 | 7/1994 | Chang . |
| 5,340,719 | 8/1994 | Hajek et al. . |
| 5,374,531 * | 12/1994 | Jensen ................................ 435/7.24 |
| 5,405,784 | 4/1995 | Van Hoegaerden . |
| 5,422,277 | 6/1995 | Connelly et al. . |
| 5,424,213 * | 6/1995 | Mougin ................................. 436/63 |
| 5,491,068 * | 2/1996 | Benjamin et al. ................. 435/7.32 |
| 5,514,340 * | 5/1996 | Lansdorp et al. .................... 422/101 |
| 5,536,644 * | 7/1996 | Ullman et al. ..................... 435/7.25 |
| 5,624,815 * | 4/1997 | Grant et al. ............................ 435/30 |

FOREIGN PATENT DOCUMENTS

| | | |
|---|---|---|
| 016 552 | 10/1980 | (EP) . |
| A1 0098534 | 1/1984 | (EP) . |
| A2 0131934 | 1/1985 | (EP) . |
| 241 042 | 10/1987 | (EP) . |
| 256 471 | 2/1988 | (EP) . |
| 129 434 | 9/1989 | (EP) . |
| A1 0339769 | 11/1989 | (EP) . |
| 403960 | 6/1990 | (EP) . |
| 395 355 | 10/1990 | (EP) . |
| 537 827 | 4/1993 | (EP) . |
| 2638849 | 5/1990 | (FR) . |
| WO 88/05309 | 7/1988 | (WO) . |
| WO 90/07380 | 7/1990 | (WO) . |
| WO 90/10692 WO A1 | 9/1990 | (WO) . |
| 9101368 | 2/1991 | (WO) . |
| WO 91/09058 WO A1 | 6/1991 | (WO) . |
| 9109938 | 7/1991 | (WO) . |
| WO 91/15766 | 10/1991 | (WO) . |
| 92/04961 * | 4/1992 | (WO) . |
| WO 94/02016 | 2/1994 | (WO) . |
| WO 94/07142 | 3/1994 | (WO) . |
| 94/07139 * WO A1 | 3/1994 | (WO) . |
| 9407138 | 3/1994 | (WO) . |
| 95/24648 | 9/1995 | (WO) . |
| WO 95/34817 | 12/1995 | (WO) . |
| WO 96/31777 | 10/1996 | (WO) . |

OTHER PUBLICATIONS

Pilling et al., "The Kinetics of Interaction between Lymphocytes and Magnetic Polymer Particles," J. of Immunol. Methods, 122:235–241, 1989.*

Rye et al., "Immunobead Filtration", Am J. Pathology, 150 (1):99–106, 1997.*

Abstract of Accession No. 90658782 Cancerlit; "Fourth International Conference on Monoclonal Antibody Immunoconjugates for Cancer"; Mar. 30 to Apr. 1, 1989, San Diego, CA, USCD Cancer Center.

Abstract of Crews J.R. et al.; *Int. Journ. of cancer*; Jul. 9, 1992; vol. 51, No. 2.

Dialog Information Service, File 159, Cancerlit, Dialog accession No. 01046200, Cancerlit accession No. 94290389, Lemoli RM et al: "Positive selection of hematopietic CD34+ stem cells provides 'indirect purging' of CD34– lymphoid cells and the purging efficiency is increased by anti–CD2 and anti–CD30 immunotoxins", Bone Marrow Transplant; 13(4):465–71, 1994.

Dialog Information Service, File 159, Cancerlit, Dialog accession No. 01018250, Cancerlit accession No. 94084695, Myklebust AT et al: "Comparison of two antibody–based methods for elimation of breast cancer cells from hman bone marrow", Cancer Res; 54(1):209–14, 1994.

Dialog Information Service, File 159, Cancerlit, Dialog accession No. 00803246, Cancerlit accession No. 91348943, Tecce R. et al: "Production and Characterization of two Immunotoxins Specific for M5B Anll Leukaemia", Int. J. Cancer'49(2):310–6, 1991.

Dialog Information Service, File 159, Cancerlit, Dialog accession No. 00447849, Cancerlit accession No. 86110672, Tonevitsky AG et al: "Elimination of Murine Erythroleukemic Stem Cells with a Novel Anti–Erythroid Antibody Conjugated to Ricin a–chain: A Model for Studies of Bone- –Marrow Transplantation Therapy", Int. J. Cancer; 37(2):263–73, 1986.

Dialog Information Service, File 159, Cancerlit, Dialog accession No. 01268628, Cancerlit accession No. 97031812, Kvalheim G. et al: "Purging of tumor cells from leukapheresis products: experimental and clinical aspects", J. Hematother; 5(4):427–36, 1996.

K.M. Stray, et al.; "Purging Tumor Cells from Bone Marrow or Peripheral Blood Using Avidin–Biotin Immunoadsorption";*Advances in Bone Marrow Purging and Processing*; 1994; Orlando: Wiley–Liss, Inc.; pp 97–103.

Hitoshi Maeda; "Applicability of an Immuno–microsphere Technique for a Forensic Identification of ABO Blood Types: The Use of Fluorescent Microspheres";*Jpn J. Legal Med.*; 1989; pp. 322–327.

Andrew J. Beavis, et al.; "Detection of Cell–Surface Antigens Using Antibody–Conjugated Fluorosphers (ACF): Application for Six–Color Immunofluorescence"; *Biotechniques*; 1996; pp. 498–503.

Derwent acession No. 93–173192, Toyobo KK: "Sensitivity detection of ligand–receptor reaction–by combining fluorescent fine particles with objective substance, passing mixt. through flow cytometer, counting number of agglomerates etc."; & JP,A,5107249, 930427, DW9321.

K.A. Muirhead, et al.; "Flow Cytometry: Present and Future"; *Biotechnology*; Apr. 1985; vol. 3, pp. 337–356.

Michael J. Bjorn, et al.; "Antibody–Pseudomonas Exotoxin A Conjugates Cytotoxic to Human Breast Cancer Cells in Vitro"; *Cancer Research*; Jul. 1986; pp. 3262–3267.

Ian c. Anderson, et al.; "Elimination of Malignant Clonogenic Breast Cancer Cells from Human Bone Marrow"; *Cancer Research*; pp. 4659–4664.

K.C. O–Briant, MS, et al.; Elimination of Clongenic Breast Cancer Cells from Human Bone Marrow; *Cancer*; 1991; pp. 1272–1278.

C.L. Tyer, et al.; "Breast Cancer Cells are Effectively Purged from Peripheral Blood Progenitor cells Using an Immunomagnetic Technique"; Abstract to First meeting of International Society for Hematotherapy and Graft Engineering, Orlando, Fl, 1993.

Fiorenzo Stirpe, et al.; "Ribosome–Inactivating Proteins from Plants: Present Status and future Prospects"; *Bio/Technology*; Apr. 1992; vol. 10, pp. 405–412.

Luigi Barbieri, et al.; "Ribosome–inactivating proteins from plants"; *Biochimica et Biophysica Acta*; 1993; pp. 237–282.

R.M. Lemoli, et al.; "Positive selection of hematopoietic CD34+ stem cells provides 'indirect purging' of CD34– lymphoid cells and the purging efficiency is increased by anti–CD2 and anti–CD30 immunotoxins"; *Bone Marrow Transplantation*; 1994; pp. 465–471.

I.J. Diel, et al.; "Detection of Tumor Cells in Bone Marrow of Patients with Primary Breast Cancer: A Prognostic Factor for Distant Metastasis"; *Journal of Clinical Oncology*; 1992; pp. 1534–1539.

W. Kemmner, et al.; "Separation of tumor cells from a suspension of dissociated human colorectal carcinoma tissue by means of monoclonal antibody–coated magnetic beads"; *Journal of Immunological Methods*; 1992; pp. 197–200.

C.I. Civin, et al.,; "Positive stem cell selection –basic science"; *Progress in Clinical and Biological Research*; vol. 333, 1990, pp. 387–402.

E.H. Dunlop, et al.; "Magnetic separation in biotechnology"; *Biotech ADVS*; vol. 2, 1984, pp. 66–69.

C.H. Setchell; "Magnetic Separations in Biotechnology– a Review"; *J. Chem. Tech. Biotechnol.*; vol. 35B, No. 3, 1985, pp. 175–182.

J.H. Pizzonia, et al.; "Immunomagnetic separation, primary culture, and characterization of cortical thick ascending limb plus distal convoluted tubule cells from mouse kidney"; *National Library of Medicine*, File Medline, Medline accession No. 07671620; Br J Haematol Mar. 1991; 77 (3), pp. 267–273.

R.M. Leven, et al.,; "Immunomagnetic bead isolation of megakaryocytes from guinea–pig bone marrow: effect of recombinant interleukin–6 on size, ploidy and cytoplasmic fragmentation"; *National Library of Medicine*, File Medline, Medline accession No. 07671620; Br J Haematol Mar. 1991; 77 (3), pp. 267–273.

G. Kvalheim, et al.; "Elimination of B–Lymphoma Cells from Human Bone Marrow: Model Experiments Using Monodisperse Magnetic Particles Coated with Primary Monoclonal Antibodies"; *Cancer Research*; vol. 47, Feb. 1987, pp. 846–851.

J.T. Kemshead, et al.; "Monoclonal antibodies and magnetic microspheres for the depletion of leukamic cells from bone marrow harvested for autologous transplantation"; *Bone Marrow Transplantation*; 1987; vol. 2, pp. 133–139.

G. Kvalheim, et al.; "Immunomagnetic purging of B–lymphoma cells from human bone marrow"; *Dialog Information service*, File 159, Cancerlit, Dialog accession No. 00559663; Fourth European Conference on Clinical Oncology and Cancer Nursing, Nov. 1–4, 1987, Madrid, Federation of European Cancer Societies, pp. 262, 1987.

T. Lea, et al.; "Monosized, magnetic polymer particles: their use in separation of cells and subcellular components, and in the study of lymphocyte function in vitro"; *National Library of Medicine*, File Medline, Medline accession No. 90234499; J. Mol. Recognit. Feb. 1988; 1(1). pp. 9–18.

Arne T. Muklebust, et al.; "Eradication of Small Cell Lung Cancer Cells from Human Bone Marrow with Immunotoxins"; *Cancer Research*; 1993; pp. 3784–3788.

William P. Peters, et al.; "High–Dose Chemotherapy and Autologous Bone Marrow Support as Consolidation After Standard–Dose Adjuvant Therapy for High–Risk Primary Breast Cancer"; *Journal of Clinical Oncology*; Jun. 1993; vol. 11, No. 6, pp. 1132–1143.

James O. Armitage, M.D.; "Bone Marrow Transplantation"; *New England Journal of Medicine*; Mar. 24, 1994; vol. 330, No. 12, pp. 827–838.

Thomas J. Moss, et al.; "Contamination of Peripheral Blood Stem Cell Harvests by Circulating Neuroblastoma Cells"; *Blood*; 1990; vol. 76, No. 9, pp. 1879–1883.

Amy A. Ross, et al.; "Detection and Viability of Tumor Cells in Peripheral Blood Stem Cell Collections From Breast Cancer Patients Using Immunocytochemical and clonogenic Assay Techniques"; *Blood*; 1993; vol. 82, No. 9, pp. 2605–2610.

Malcolm K. Brenner, et al.; "Gene–marking to trace origin of relapse after autologous bone–marrow transplantation"; *Lancet*; 1993; pp. 85–86.

John G. Gribben, M.D., et al.; "Immunologic Purging of Marrow Assessed by PCR Before Autologous Bone Marrow Transplantation for B–Cell Lymphoma"; *New England Journal of Medicine*; Nov. 28, 1991; vol. 325, No. 22, pp. 1525–1533.

Elizabeth J. Shpall, et al.; "Release of Tumor Cells from Bone Marrow"; *Blood*; Feb. 1, 1994; pp. 623–625.

Wolfram Brugger, et al.; "Mobilization of Tumor Cells and Hematopoietic Progenitor Cells Into Peripheral Blood of Patients With Solid Tumors"; *Blood*; 1994; vol. 83, No. 3, pp. 636–640.

Ger J. Strous, et al.; "Mucin–Type Glycoproteins"; *Critical Reviews in Biochemistry and Molecular Biology*; 1992; pp. 57–92.

Lou de Leij, et al.; "The Use of Monoclonal Antibodies for the Pathological Diagnosis of Lung Cancer"; In; H.H. Hansen (ed), Lung Cancer: Basic and Clinical Aspects; Boston: Martinus Niijhoff Publishers, 1986; pp. 31–48.

Aslak Godal, et al.; "Immunotoxins directed Against the High–Molecular–Weight Melanoma–Associated Antigen. Identification of Potent Antibody–Toxin Combinations"; *Int. J. Cancer*; 1992; pp. 631–635.

V.D. Courtenay, et al.; "An In Vitro Colony Assay For Human Tumours Grown in Immune–Suppressed Mice and Treated In Vivo with Cytotoxic Agents"; *Br. J. Cancer*; 1978; pp. 261–268.

M.Y. Wang, et al.; "An effective immunomagnetic method for bone marrow purging in T cell malignancies"; *Bone Marrow Transplantation*; 1992; pp. 319–323.

Arne T. Myklebust, et al.; "Comparison of Two Antibody––based Methods for Elimination of Breast Cancer Cells from Human Bone Marrow"; *Cancer Research*; 1994; pp. 209–214.

Connie J. Eaves; "Peripheral Blood Stem Cells Reach New Heights"; *Blood*; 1993; pp. 1957–1959.

Elizabeth J. Shpall, et al.; "Transplantation of Enriched CD34–Positive Autologous Marrow Into Breast Cancer Patients Following High–Dose Chemotherapy: Influence of CD34–Positive Peripheral–Blood Progenitors and Growth Factors on Engraftment"; *Journal of clinical Oncology*; 1994; vol. 12, No. 1, pp. 28–36.

Bio/Technology, vol. 11, Bjorn–Ivar Haukanes et al., "Application of Magnetic Beads in Bioassays" p. 60–63, Jan. 1993.

Scand J. Immunol, vol. 31, J. Heldrup, "A New Technique Using an Aggregating Antibody Against Glycophorin in–A for Puring Ficoll–Paque–Separated Leugocytes of Contaminating Erythroid Lineage Cells", p. 289–p. 296, see "Materials and methods" and p. 295, right column.

* cited by examiner

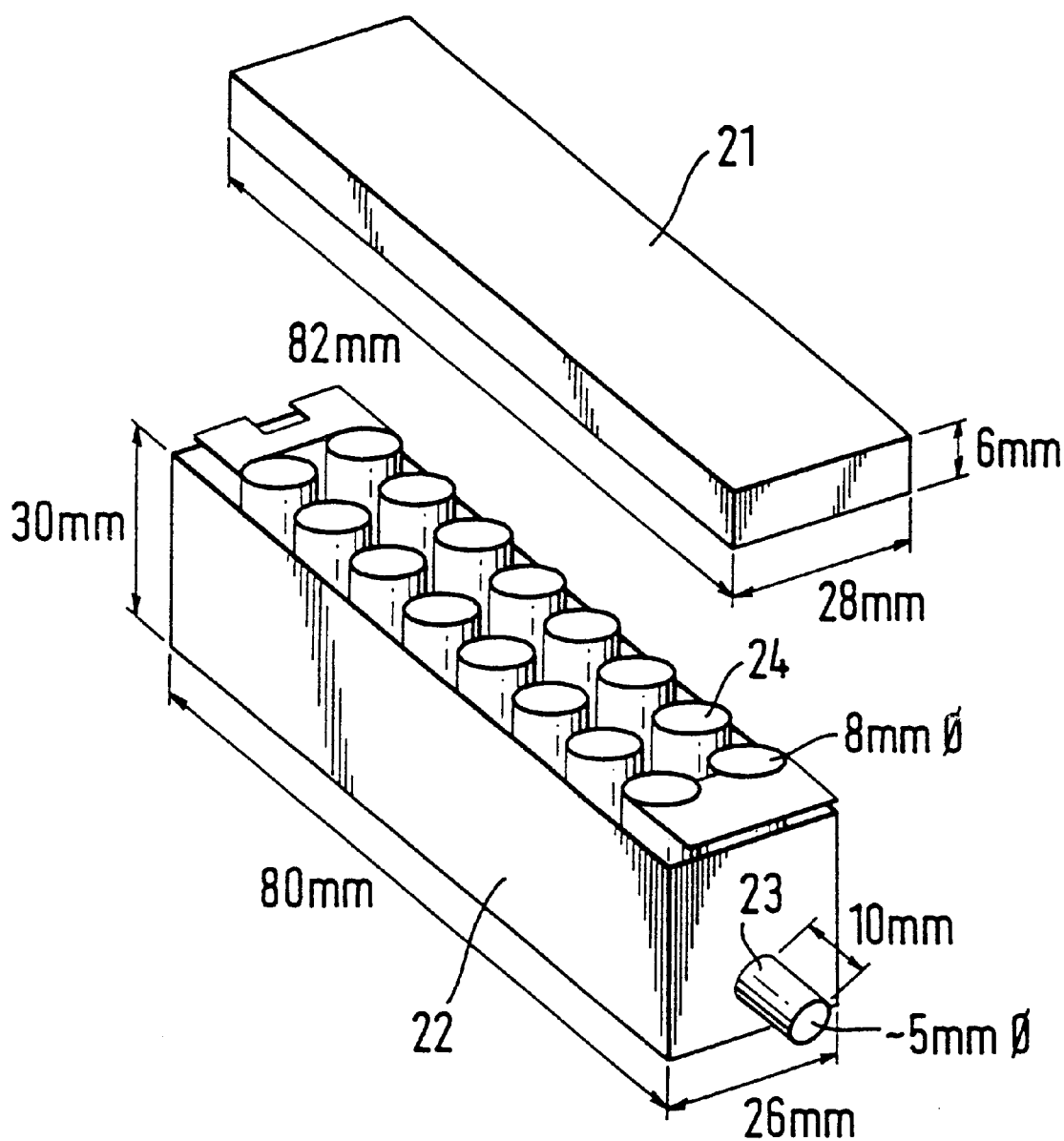
Fig. 1.1

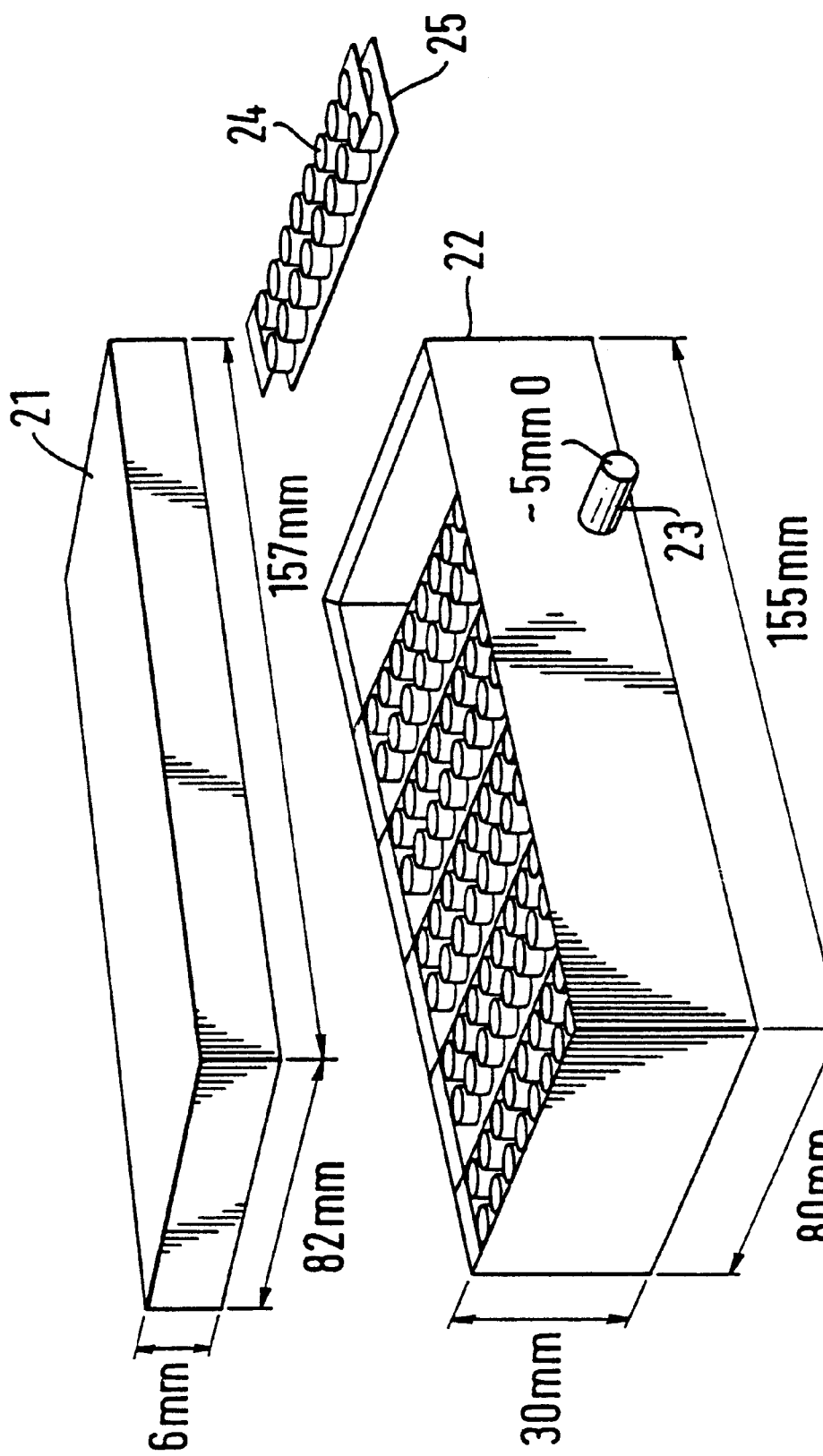
Fig.1.2

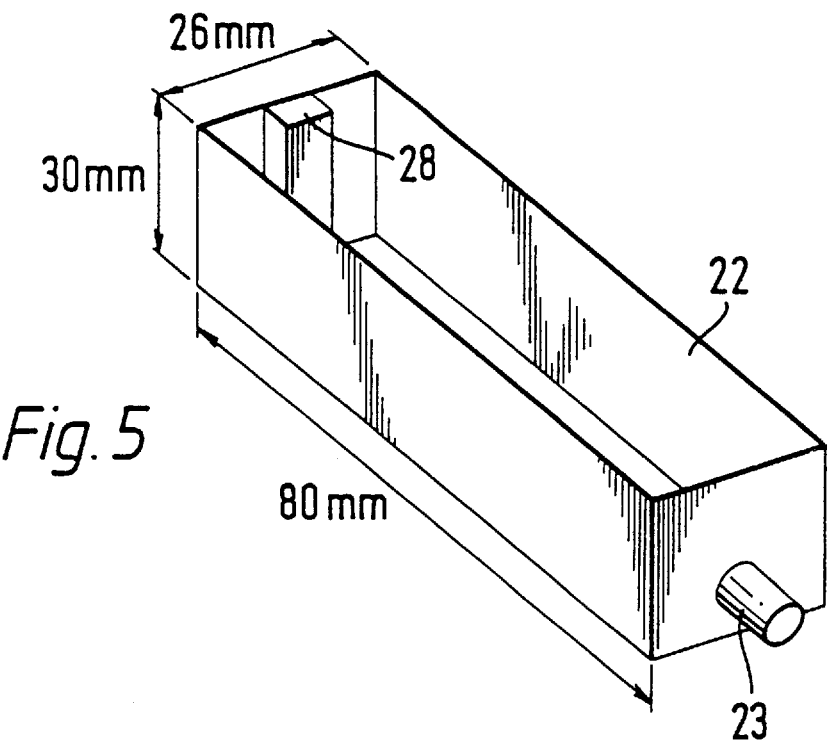
Fig. 5
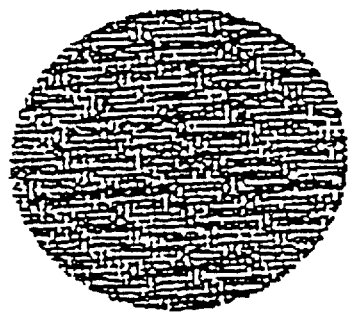
10 CELLS
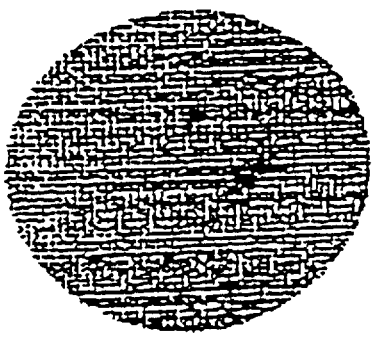
100 CELLS
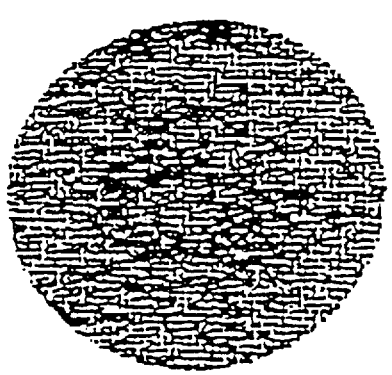
1000 CELLS
Fig. 6

METHOD AND DEVICE FOR DETECTION OF SPECIFIC TARGET CELLS IN SPECIALIZED OR MIXED CELL POPULATIONS AND SOLUTIONS CONTAINING MIXED CELL POPULATIONS

CROSS-REFERENCE TO RELATED APPLICATIONS

The present application claims priority of PCT/NO95/00052, filed Mar. 10, 1995, now WO 95/24648, and Norwegian application no. 940866, filed Mar. 10, 1994.

The present invention relates to an immunomagnetic method for detection of specific target cells in cell populations and solutions of cell populations. The invention also relates to a kit and apparatus for performing the method in different cell populations.

In biology, biochemistry and adjacent fields there is considerable need for methods in which chemical entities are linked together. Such methods have an increasing importance in research regarding both normal and abnormal cell populations. Especially when solid supports are used cells can be immobilized, detected and isolated and purified. Furthermore, the cell content may be examined using a range of sophisticated methods. It is also of importance to be able to isolate the cells in viable forms.

Affinity binding is a sophisticated way of linking chemical/biochemical entities together. In such a method a pair of binding partners, which for example are attached to the substances to be linked, bind to each other when brought in contact. One of the binding partners in such a linkage may be represented by a molecule on the cell surface. Several such binding partner systems are known, such as antigen-antibody, enzyme-receptor, ligand-receptor interactions on cells and biotin-avidin binding, of which antigen-antibody binding is most frequently used.

When such methods are used for isolation of specific cells, which are the subject for farther various examinations it is necessary that the cells should recover their function upon returning to the original conditions. This is not always the case, although it is proposed a method for providing physiological conditions such that the isolated specific cells can develop in sufficient numbers to allow further characterisation.

Methods are known in which one of the binding partners is attached to an insoluble support., such as paramagnetic particles, and by which isolation of target cells in a mixed cell population is performed as negative isolation or positive isolation. In a negative isolation procedure the unwanted cells can be removed from the cell preparation by incubating the cells with antibody-coated particles, specific for the unwanted cells. Following the incubation the cell/antibody/particle complex can be removed using the particles, leaving the wanted target cells behind. This result is often not satisfactory, since the wanted cells are left in the cell population, more or less purified, and also since the intention of the isolation procedure is to examine and/or perform further studies on the specific target cells. Attempts have been made to use particles for positive isolation, in which the wanted target cells are removed from the mixed cell population. These procedures have, however, been directed to certain target cells and are not suited for all target cell systems. A positive isolation procedure involving the hapten/anti-hapten linkage system has recently been proposed (WO91/01368) and relates to a method of connecting target cells to an insoluble support by using the abilities of hapten, antihapten antibodies and anti-cell antibodies to bind to each other, thus constructing a linkage between the insoluble support. i.e. particle, and the target cell, consisting at least of hapten and anti-hapten antibody or combinations of hapten and anti-hapten antibodies and anti-anti-hapten antibodies or secondary anti-cell antibodies. The later cleavage of the complex is performed by again exposing it to hapten or hapten analogue. Thus the constructed link always consists of hapten in addition to 1 or more elements. The method is directed to unspecified target cells and is directed to isolation of target cells and release of the insoluble support.

Furthermore, WO91/09938 describes the use of a combination of positive and negative selection for the purpose of isolating and possibly growing specific cells, i.e. haematopoietic progenitor cells, in the bone marrow, and is dependent upon removal of the particles. WO92/04961 comprises a method and a complicated equipment to separate cells or different molecules from a non-magnetic test medium by using colloidal magnetic paricles. In this method small (sub micron) particles are used because it is necessary to avoid precipitation of the particles in the solution and this method necessitates complicated apparatus, in which magnetic intensifying means is immersed in the test medium. This may have adverse effects on the cells.

In "Application of Magnetic Beads in Bioassays", B. Haukanes and C. Kvam. Bio/Technology, 11:60–63. 1993,. several methods are described for use of magnetic particles to remove tumor cells from bone marrow, isolation of lymphoid cells from peripheral blood and isolation of DNA, RNA and DNA-binding proteins. All described methods have specificities which are unsuitable for the present purpose of detecting only target-cells. The above methods will in addition to target cells also bind non-target cells due to cross-reactivity and unspecific adhesion of the antibody-particle complex.

There is also described a multiwell filtration apparatus for the assay of microliter quantities (EP-A-0 098 534), a filter strip and composite assemblies for filtering microliter quantities of fluid (EP-A-0 339 769) and an assay cartridge which has a substantially rectangular base plate, a substantially rectangular top plate and four side walls (EP-A-0 131 934). None of the above apparatus are applicable for the present purpose in that they describe pore sizes which are too small for the present purpose of retaining only particle-cell rosettes. Furthermore the filters are not designed to be exposed to several examinations of the retained cells without removing them form the filter medium.

There is a need for a simple linkage to connect a target cell to an insoluble support, which does not involve compounds of a rather unspecified hapten-group, and which is directed to detection of specific target cells, with a mini-mum of unspecific cell association and which render unnecessary a later cleavage between the insoluble support and the specific target cell.

In a co-pending application by one of the applicants (WO94/07 139, filed Sep. 10, 1993) a method is described for detecting diagnostic purposes specific target cells without the problem with unspecific binding to normal cells. They represent sensitive detection methods for a variety of cell types, such that a high number of cells can be readily screened in the microscope and the procedure is rapid and simple. Furthermore, the methods can be used for isolation of cells for biochemical, biological and immunological examination, and for studying of specific genes at the nucleotide or protein level, in addition to culturing the cells, without the need for cleaving the cell-particles complex.

There is, however, a need for improvements such as isolation of the particle-bound target cells in the target cell suspension, from unbound beads, unspecifically bound non-target cells and unbound non-target cells, which is simple to perform, not time requirering and with render the target cell/particle complexes suitable to perform further analysis such as for example microscopic examinations and growing in a culture medium.

BRIEF SUMMARY OF THE INVENTION

These objects are obtained by the present invention outlined by the method, apparatus and kit characterised in the enclosed claims.

The method for immunomagnetic detection of target cells in a mixed cell population and physiological solutions containing cell populations is suitable for detection, but may also be used in positive isolation of specific types of both normal cells and pathogenic cells. The method creates a linkage between a specific target cell and an insoluble support, such as paramagnetic particles, which consists of one or two elements. The particle is either coated with an anti-cell antibody of murine or human origin, directed to the specific antigen determinants in the membranes of the wanted target-cells, or the particles are coated with a polyclonal anti-mouse or anti-human antibody capable of binding to the Fc-portions of the specific anti-cell antibody directed to the antigen determinants in the target-cell membranes. Instead of using the polyclonal anti-mouse/anti-human antibody for coating the particles, a monoclonal rat anti-mouse/anti-human antibody may be used. This last antibody, due partly to its monoclonal origin, may provide a more specific binding to the anti-cell antibody and reduce the risk for possible cross-reactions with other cells in solutions, such as blood. Furthermore, incubation of the cell suspension with a mild detergent and/or second set of antibodies or antibody fragments, prelabeled or not with fluorescent agents, metallocolloids, radioisotopes, biotin-complexes or certain enzymes allowing visualization, will dramatically increase the specificity of the method.

Furthermore, according to the present invention, the method can be profoundly improved and simplified by transfering the supension of target cell/particle complexes to the cell filtering device or cell separator according the present invention and the total number of target cells viewed microscopically or grown in a physiologically base culture medium to be characterised for the presence of specific biochemical and biological features.

BRIEF DESCRIPTION OF THE DRAWINGS

Of the drawings:

FIG. 1.1. shows a perspective view of an embodiment of the cell filtering device or Cell Separator, partly assembled.

FIG. 1.2. shows a perspective view of another embodiment of the Cell Separator, partly assembled.

FIG. 5. shows a perspective view of a version of the Cell Separator Fitrate Collection Box.

FIG. 6. show melanoma cell-particle rosettes entrapped on cell filter device using the method described.

DETAILED DESCRIPTION

Figure 2:
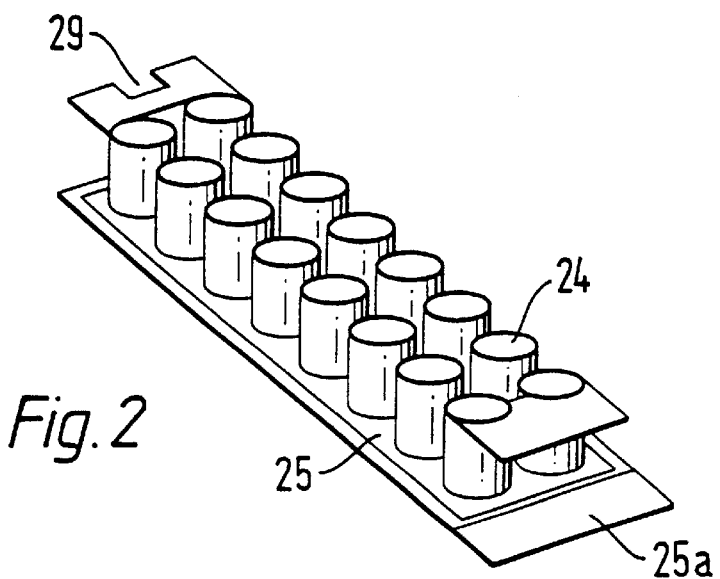
FIG. 2. shows a perspective view of a version of the Cell Separator Multiwells wit FIG. 3. shows membrane Filter detached from the Multiwells.
Figure 3:
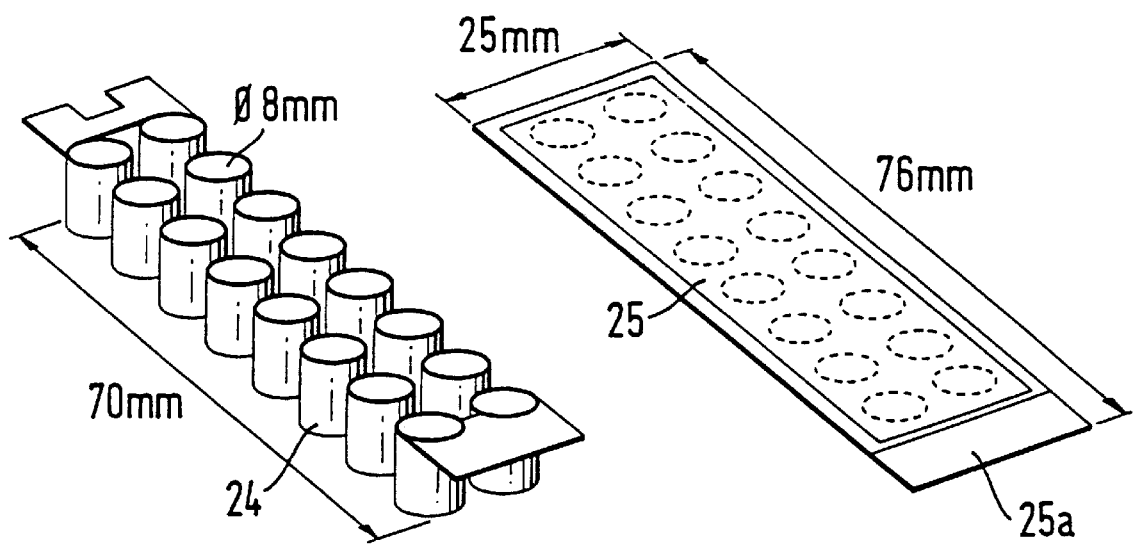
Figure 4:
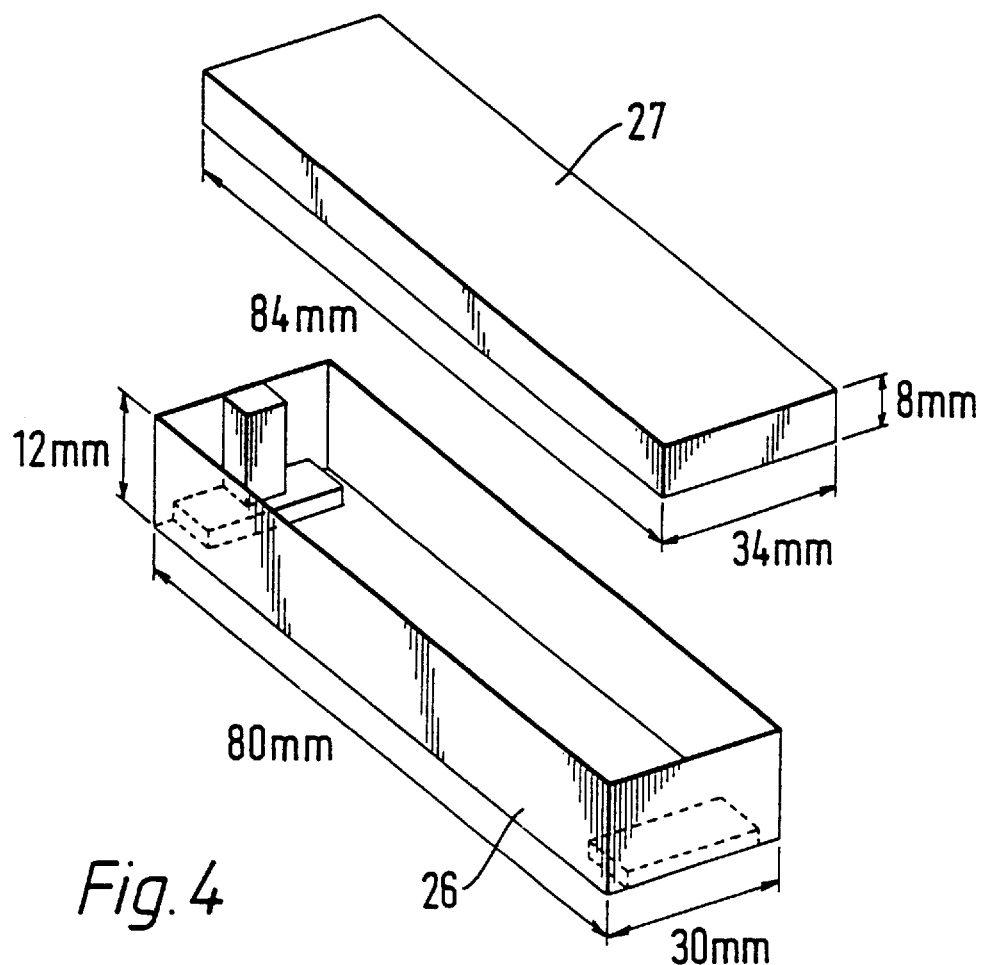
FIG. 4. shows a perspective view of a version of the culture dish with lid arrangement for the Cell Separator Multiwells and/or the Membrane Filter.
Figure 4A:
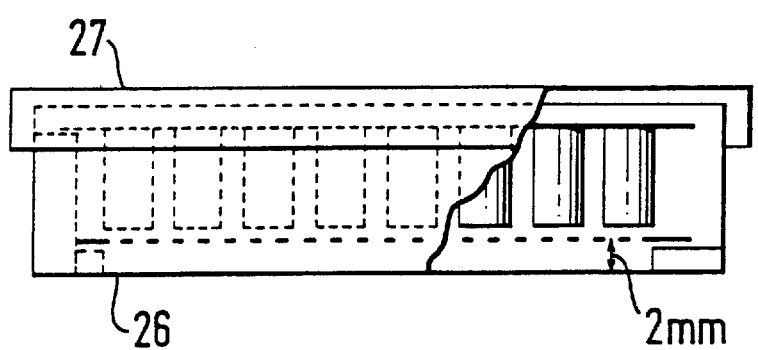
FIG. 4a. shows a side elevation of the Multiwell arrangement in the culture dish.

In the following a more detailed disclosure of the method is presented, using cancer cells as the target-cells for detection and possible isolation. The method is, however, not limited to cancer cells and the disclosure shall not limit the method to this particular field of use, since the method is suitable within a range of cytological research areas.

In the management of cancer patients, the staging of the disease with regards to whether it is localized or if metastatic spread has occurred to other tissues, is of utmost importance for the choice of therapeutic alternative for the individual patient. Malignant cells spread by direct invasion into the surrounding tissue, through the lymphatics or by the distribution of tumor cells in the blood to distant organs, including the bone marrow and the central nervous system and the cerebrospinal fluid.

Detection of metastatic tumor cells has, until recently, relied on morphological methods using light and electron microscopy on biopsied tumor specimens, on smears of bone marrow and peripheral blood, and on slides prepared after cyto-centrifugation of various body fluids. Since the advent of monoclonal antibodies recognising antigens predominantly expressed on the surface of different types of malignant cells, the identification of metastatic cells has, to an increasing extent, also involved immunocytochemistry and immunofluorescence. Thus, slides prepared from biopsied tumors or cyto-centrifugation have been treated with monoclonal antibodies, and the binding of these to the tumor cells is visualized calorimetrically or by fluorescence. The latter method requires the use of a fluorescence microscope, alternatively preparing a cell suspension and use of a flow cytometer.

The previous methods suffer from limited sensitivity and/or specificity, and is usually laborious and time consuming, also requiring a high degree of expertise. Flow cytometric examinations also involve expensive equipment.

The morphological methods for the detection of tumor cells in blood and bone marrow are much less sensitive than methods involving immunocytochemistry and immunofluorescence. Also the latter methods are, however, inadequate in cases where the tumor cells represent less than 1% of the total number of nucleated cells. Flow cytometry may provide better sensitivity than the methods involving the use of a microscope, but requires the availability of a high number of cells, and also involves several technical difficulties. Thus, aggregation of cells may cause problems, and the method does not provide possibilities to distinguish between labeled tumor cells and unspecifically fluorescing normal cells.

The invention allows for a very sensitive detection of, for example, metastatic tumor cells, since a large volume and high number of cells can readily be screened in the microscope and the attached magnetic beads are easily recognisable. The method and apparatus described provides a solid support and permenant record which is easily viewed by microscopy, permits assessment and quantification of the whole specimen rather than small fractions thereof and allows the use of large specimen volumes to be analysed, the device may also be scanned automatically by conventional densitometric technology. The monoclonal antibodies used bind with sufficient specificity to, for example, tumor cells and not to other cells than the target cells present in mixed cell suspensions, like blood, bone marrow, and in other tumor manifestations, such that all cells with attached beads represent the target-cells. In addition, the procedure is rapid and simple, and can be performed by any investigator with access to a conventional microscope.

The novel method involves the binding of monoclonal antibodies, e.g. of murine or human origin, that specifically recognize antigens present on tumor cells, and not on the normal cells in question, or for other purposes to specified subpopulations of normal cells, to paramagnetic particles, either directly or to beads first covered with antibodies specifically recognizing the respective antibodies, or the Fc-portion of IgG antibodies, that bind to the tumor cells. The cell binding antibodies may be of the IgG or IgM type or being a fragment of ab IgG or IgM. Examples of used anti-target-cell antibodies may be those directed against groups of antigen determinants, for example CD56/NCAM antigen (MOC-1), Cluster 2 epithelial antigen (MOC31), Cluster 2 (MW-40 kD) antigen (NrLulO) (Myklebust et al. Br. J. Cancer Suppl. 63, 49–53, 1991), HMW-melanoma-associated antigen (9.2, 27) (Morgan et al., Hybridoma, 1, 27–36, 1981), 80 kD, Sarcoma-associated antigen (TP1 & TP3) (Cancer Res. 48, 5302–5309, 1988), mucin antigens (Diel et al., Breast Cancer Res. Treatm., 1991), or EGF-receptor antigen (425.3) (Merck), in addition to the anti-pan-human antibody (Bruland et al., unpublished), which is suitable for detecting human cells among animal cells. The 425.3 antibody is directed towards antigens in both normal and malignant cells. Antibodies can furthermore be directed against growth factor receptors, for example EGF-receptor, PDGF (A and B) receptor, insulin receptor, insulin-like receptor, transferrin receptor, NGF and FGF receptors, group of integrins, other adhesion membrane molecules and MDR proteins in both normal cells and abnormal cells, and antigens present on subpopulations of normal cells, in addition to oncogenic products, expressed on the membranes of normal and malignant cells and on malignant cells alone, for example Neu/erb B2/HER2. As for the malignant cells, these may be breast, ovarian and lung carcinoma cells, melanoma, sarcoma, glioblastoma, cancer cells of the gastrointestinal tract and the reticuloendothelial system, or the target-cells may be associated with non-neoplastic diseases, such as cardiovascular, neurological pulmonary, autoimmune, gastrointestial, genitourinary, reticuloendothelial and other disorders. Furthermore, the malignant cell population may be located in bone marrow, peripheral blood, come from pleural and peritoneal effusions and other body fluid compartments, such as urine, cerebrospinal fluid, semen, lymph or from solid tumors in normal tissues and organs, for example liver, lymph nodes, spleen, lung, pancreas, bone tissue, the central nervous system, prostatic gland, skin and mucous membranes. A more complete list of the antigen determinants and the corresponding antibodies or antibody fragments used in the present improved method is presented in Table 1.

Methodology

The method comprises attachment of the antibodies directly to the paramagnetic particles, or the attachment can take place by attachment to surface-bound antibodies, such as polyclonal anti-mouse antibodies, monoclonal rat anti-mouse antibodies or monoclonal anti-human antibodies, specifically recognizing the Fc-portion of the said individual antibodies. The antibodycoated paramagnetic beads are then mixed with the suspension of cells to be examined and incubated for 5–10 min to 2 h, preferably for 30 min at 0–25C., preferably at 4C., under gentle rotation. The present method may also be performed in a changed order of steps, in that the free target-cell antibodies are added to the cell suspension, incubated for 5–10 min to 2h, preferably 30 min, at 0–20C., preferably 4C., under gentle rotation. The paramagnetic particles, precoated with anti-mouse or anti-human antibodies are then added to the incubated cell suspension, as described above, and the resulting suspension subjected to a further incubation of 5–10 min to 2 h, preferably 30 min, at 0–25C., preferably 4C. under gentle agitation. The present method may also be performed in an abbreviated number of steps, in that the free target-cell antibodies are added to the cell suspension, at the same time and together with the precoated paramagnetic particles and subjected to incubation of 5–10 min to 2 h, preferably 30 min, at 0–25C., preferably 4C. under gentle agitation. The number of antibody-coated beads added to the cell suspension should be between 0.5–10 times the number of target cells. When this number is unknown, the amount of coated beads added should be 1–10% of the total number of cells. For specific purposes, and in the cases where the density of the target-cells is low, for example malignant cells, or the target-cells represent a very low fraction of the total number of cells (about 1%), the target cells can be positively separated from non-target cells in a magnetic field. The isolated target cells, in cell suspension may then be transferred to a cell counting device, and the number of cells with attached beads may be determined by microscopy. The present method may also be performed, and preferably so, by transferring the isolated target cell suspension to the cell filtering device described in this application, and the total number of isolated target cells viewed by microscopy. The isolated target cells in the filter device may be fixed and stained to facilitate viewing by light microscopy. For specific purposes and in cases where the isolated target cells are required to be functionally active, a physiologically based culture medium may be added to the cell filter device and subjected to incubation for an unspecified time at 37C. The isolated target-cells may be grown and subsequently characterised for the presence of specific biochemical and biological features. Moreover, the target-cells may be characterised for the presence of specific biochemical and biological features. Of particular importance will be the use of such cells for studies in molecular biology. In contrast to the above cited methods of the prior art, the present method allows studies and growth of the target-cells without performing a cleavage of the paramagnetic particle-target cell linkage. For several purposes it is of interest to examine specific genes in a pure population of target cells at the DNA, mRNA and protein level, both in tumor biopsies as well as in tumor cells present in blood, bone marrow and other body fluids, for example urine, cerebrospinal fluid, semen, lymph, or from otherwise normal tissues and organs, for example liver, lymph nodes, spleen, lung, pancreas, bone tissues, central nervous system, prostatic gland, skin and mucous membranes, and in other areas of cytological research activity. With the methods of prior art, signals obtained on Southern, Northern and Western blots represent the normal cells as well as the tumor cells in the biopsy. If a single cell suspension is first prepared from the tumor material, and the tumor cells are then positively immunomagnetically detected and separated, any gene studies performed on this material would represent the target-cells only. This also relates to for example malignant cells present in mammalian tissues, for example in bone marrow, peripheral blood, pleural and peritoneal effusions, and other body fluids, for example urine, cerebrospinal fluid, semen and lymph. Studies involving polymerase chain reaction (PCR) methodology will also gain in specificity and reliability when performed on pure tumor cell populations obtained by the new method.

The application of the new method steps may differ depending on type of tissues to be examined.

a) Tissue from solid or needle tumor biopsies is prepared mechanically or with mild enzymatic treatment into a single cell suspension, to which the primary, specific antibodies or antibody fragments are added directly or after washing the cell suspension with phosphate buffered saline or culture medium with or without serum, such as fetal calf serum, bovine, horse, pig, goat or human serum.

b) If the material is a sample of pleural or ascitic effusion, cerebrospinal fluid, urine, lymph or body fluids such as effusions in the joints of patients with various forms of arthritis, the specific antibodies or antibody fragments are either added to the samples directly, or after centrifugation with or without washings before or after the cells in the samples are spun down and brought back into suspension, c) If the material consists of blood or bone marrow aspirate, the specific antibodies or antibody fragments are either added to the samples directly, or after centrifugation with or without washings before or after the cells in the samples are spun down and brought back into suspension, or a mononuclear cell fraction may be prepared by gradient centrifugation on e.g. Lymphoprep before washing, resuspension, and addition of the appropriate antibodies or antibody fragments.

The procedure conditions for a) and by are established, as exemplified by results obtained in successful experiments as those described below.

For c) the results have been found to be influenced by a high number of factors which have been examined in detail. Among these are antibody concentration, the ratio of the number of paramagnetic particles versus number of cells, incubation times and volumes, type of incubation medium, and the pH level. The particle to mononuclear cell ratio in all experiments should be in the range of 0.5/1–2/1, depending on the binding affinity of the primary specific antibodies or fragments.

A major problem has been unspecific attachment to normal blood or bone marrow cells of particles coated with either sheep or rat anti-mouse antibodies alone. or in addition with the specific antibodies. Experiments have shown that the unspecific binding is equally high without the presence of the specific antibodies, indicating that the problem is not caused by crossreactivity of the targeting antibodies to normal cells. The possibility that the less than optimal specificity could be caused by ionic binding has been ruled out. Another possibility was that subpopulations of normal cells of the B-lineage might adhere to the particle-antibody complexes. However, immunomagnetic removal of B-cells from the cell suspension before adding the specific antibodies/antibody-particle complexes did not improve the specificity of the latter.

The problem with the procedure used on isolated mononuclear fractions of bone marrow and peripheral blood, that some non-target cells might also bind paramagnetic particles, has been circumvented or overcome. Thus with sheep-anti-mouse antibody coated particles alone or with specific antibodies the number of particles unspecifically attached to a low fraction mononuclear blood or bone marrow cells was reduced from an average of 10 to about 1 and in parallel the fraction of normal cells with particles decreased from 1–2% to 0.5–1% or less.

Evidence has been obtained that the problem may be caused by hydrophobic forces associated with the antibodies bound to the paramagnetic particles. Methods for reducing this hydrophobicity is thus claimed. One such method is pre-incubation of the antibody-coated particles and the cell suspension with mild detergents in suitable concentrations, for example Tween 20™ in concentrations of less than 0.1% for 30 minutes at 4C. When possible selection of the target cells is warrented, the cell suspension should contain a low concentration of the detergent, e.g. 0.01% of TWEEN 20™ polyoxyethylenesorbitan monolaurate. In several experiments this procedure has almost eliminated or dramatically reduced the problem of unspecific binding seen with the mononuclear cell fractions from blood or bone marrow.

The other improvement which, if found warranted, may be used together with the detergent step as follows:

After incubation of the cell suspension with the primary antibodies or antibody fragments and the antibody-coated paramagnetic particles as described in previously, the cell suspension is incubated with a second set of antibodies or antibody fragments directed against other extracellular or against intracellular determinants of the target cells, with or without pre-treatment with cell fixatives such as formaldehyde or alcohols. These antibodies or their fragments should have been prelabeled by fluorescent agents, metallocolloids, radioisotopes, biotin-complexes or enzymes like peroxidase and alkaline phosphatase, allowing visualization by per se known methods in the microscope and/or a suitable counting device.

The target cells will both be visualized with the latter method and have bound particles to their surface, and can thus be enumerated.

To simplify the distinction between non-target and target cells, the cell suspension, or part thereof, can before the second visualization step either be subjected to cytospin centrifugation or portions of the suspension are attached to coated glass slides on which the particle-bound cells will be spread out in a thin layer, facilitating the recognition of the double-"stained" cells.

An alternative method according to the present invention to further simplify the distinction between non-target and target cells comprises the cell filter device, wherein the whole cell suspension after the target cell selection steps, can be added directly to the cell filter device. The free unbound beads, unspecifically bound non-target cells, and any unbound non-target cells, will pass through the filter leaving the bound target cells to be visualized on the filter. The filter with the isolated target cells can be removed from the device and the cells may be fixed and stained using known immunohistochemical methods and viewed by microscopy. After the filter has been removed from the device it can be treated as a conventional microscope slide of the type that is known and normally used in immunohistochemistry.

For specific purposes the filter may either be removed from the device or remain integral to the device, and a culture medium added, such as any known culture medium with or without agarose, for the purpose of propagating the isolated target cells situated on the filter.

For use in the new procedure, kits will contain for example precoated paramagnetic particles prepared for each monoclonal antibody. In another embodiment the kits contain paramagnetic particles pre-coated with IgG isotype specific anti-mouse or anti-human antibody as one part of it, and different target cell-associated, for example tumor cell, antibodies as another part. In a third embodiment the kit contains paramagnetic particles precoated with specific anti-Fc antibodies, such as polyclonal anti-mouse, or monoclonal rat anti-mouse, or anti-mouse, or anti-human antibodies, capable of binding to the Fc portion the target-cell associating antibodies, bound to specific anti-target-cell antibodies. In a fourth embodiment the kits contain distinctive particles of a paramagnetic or non-magnetic nature, which may be coated or uncoated with a target-cell antigen or group of target-cell antigens, such that when processed by the method these particles become entrapped in the cell filter device, thereby acting as a control in demonstrating for example that all aspects of the antibody-antigen interactions in the method are working correctly. These particles may be incorporated into the cell suspension at a stage before or during the method, or the particles may be used as a separate "cell suspension" to be processed using the same method as the cell suspension comprising the target cells to be separated. In a further embodiment the kit contains other specific antibodies or antibody fragments directed against antigens/ receptors within or on the wanted target-cells, where said antibodies or antibody fragments are conjugated to peroxidase, alkaline phosphatase, or other enzymes, together with relevant substrates to such enzymes, or where said antibody or antibody fragment is bound to non-paramagnetic particles with specific colours or with bound enzymes such as peroxidase and alkaline phosphatase.

Apparatus

The new feature of the method concerns a cell filter device, which may also be termed a multiwell cell separator, and may or may not be a part of the kit as described. The device concerns a microwell cell separator arrangement, which is used to separate mixed populations of different sized cells, such as those found in blood or bone marrow. The resulting cells can be viewed directly on the membrane by microscopy or automated scanning devices. This invention may be used in conjunction with conventional magnetic particle cell isolation techniques to provide a rapid, sensitive, and simple method for screening large numbers of high or low volume samples for the presence of tumour cells within 1 to 4 hours.

According to the present invention there is provided a microwell cell separator arrangement comprising an open topped filtrate collection box, which may or may not have an attachment for a vacuum tube, and has a removable and disposable multiple wells arrangement with a cell separating membrane filter which forms the base of these multiple wells. A lid or cover to this arrangement may also be provided for.

The filtrate collection box and lid arrangement may be made from a material suitable for high temperature sterilisation, or may be made from a plastic transparent or opaque plastic material such as is known for tissue culture plastic wares.

The cell separating membrane filter may comprise a regular and consistent pore shape and size, such as is found in nylon monofilament membranes, which forms the base of the individual wells. The cell separating membrane filter may be secured to the microwells such that it can be removed after the cell separation method in order to facilitate examination. The cell separating membrane may also comprise a card or plastic surrounding frame to facilitate examination after removal from the microwells.

The filtrate collection box may comprise a frame in which removable strips of more than one well may be inserted.

The filtrate collection box may be fashioned similar to a conventional 96-well plate adapted to accommodate the cell separating membrane, collection box and low pressure vacuum attachment.

The invention may also comprise an upper lid or cover.

A disposable culture dish with lid is provided for in the device that allows the microwell strips to be inserted and cultured aseptically. Integral to the culture dish are indentations or notches that facilitate the positioning of the microwell strip similar to that in the filtrate collection box, and to prevent movement of the microwell strip during culture. The indentations or notches as described may or may not also provide for the location of the cell separating membrane after removal from the microwell strip.

The invention will be further apparent from the following description with reference to the figures of the accompanying drawings, which show, by way of example only, one form of the microwell cell separator arrangement embodying the same.

Referring to FIGS. 1.1, 1.2, 2, 3, 4.1, 5, and 6 of the drawings it will be seen that the Microwell Cell Separator arrangement 20 consists of a lid or cover 21 and a filtrate collection box 22, which may or may not have a low pressure vacuum attachment port 23, with removable Multiwell strips 24 which have a detachable membrane base 25 with support 25a.

FIGS. 1.1. and 1.2. shows two alternative embodiments of the invention partially assembled.

The filtrate collection box 22 may be similar in some respects to conventional 96-well plate formats with removable well strips, and may be arranged to fit one or multiple strips of wells.

The Multiwells 24 may be arranged in double strips as shown or in single or multiple strips.

The engagement of the Multiwells 24 in the Filtrate Collection Box 22 is such that only one orientation is possible, which may be provided for by locating pins 28 or notches 29.

The Cell Separator Membrane Filter 25 is fixed to the bottom of the Multiwells 24 and forms the base of the wells. The fixing of the membrane filter 25 to the Multiwells 24 is such that they can be separated without deformation of the membrane filter 25 or the membrane filter support 25a.

The membrane filter 25 can be viewed by microscopy or may be scanned by is densitometric or similar methodology.

The membrane filter 25 may comprise a regular and consistent pore shape and size, such as is found in nylon monofilament membranes, which forms the base of the individual wells, and may be of 5–75 $\mu$m pore size but preferably 20 $\mu$m.

The Multiwells 24 within or without the Filtrate Collection Box 22 may also be made of a material suitable for tissue culture purposes, which may also be suitable for viewing in conventional 96-well plate scanning or plate reading machines.

The culture dish 26 and culture dish lid 27 may also be made of a material suitable for tissue culture purposes. In this way it is possible to supply culture medium both through the top of the multiwells and in the bottom of the culture dish 26.

All dimensions shown in the figures are exemplary and the cell filtering device 20 should not be limited by these dimensions. Furthermore, it will be appreciated that it is not intended to limit the invention to the above example only, many variations being possible without departing from the scope thereof. The present method will in the following be illustrated by model experiments, examples of the usefulness of the new method and examples of practical applications. These examples shall not be regarded as in any way limiting the invention.

Model Experiments

1. Binding of antibody-bead complexes to tumor cell lines. To determine antibody 5 concentrations and optimal conditions for the binding of antibody-paramagnetic particle complexes to tumor cells, a large panel of cancer cell lines was used. The paramagnetic beads were bound to the cells, either by coating the specific antibodies to sheep-anti-mouse antibody (SAM)-coated paramagnetic particles, or by first incubating the cells with the specific antibodies, washing, followed by a second incubation with SAM-coated particles. The results of these experiments are given in Tables 2a and 2b, in which + indicates binding of several beads to all cells, (+) indicates either a lower number of beads bound to each cell, or that not all the tumor cells had beads attached to their surface, whereas reflects no binding, and (−) indicates very weak binding.
2. Detection of tumor cells in the mononuclear fraction of bone marrow or peripheral blood. Model experiments were performed where specific antibodies and SAM-coated paramagnetic particles were added either to such mononuclear cells or to a cell suspension where a different number of cancer cells from in vitro cultivated cell lines were added to said mononuclear cells. In some experiments, either the mononuclear cells, or the malignant cells were prestained with a fluorescent dye, to be able to distinguish between the two types of cells. In all experiments, non-binding primary antibodies, and/or sheep-anti-mouse antibody-coated beads were used separately as controls. Additional experiments without the preparation of a mononuclear cell fraction of peripheral blood were performed. It was found that the separation of cells in this way reduced the amount of unspecific binding compared to the Lymphoprep separated blood fractions.
3. Separation and visualisation of antibody-bead complexes to tumor cell lines using the cell filter device. The tumor cell suspensions and fluorescent labelled tumor cells mixed with blood or bone marrow suspensions were prepared and treated as described in the model experiments 1. and 2., and were subjected to the cell filter device. After washing, fixing and staining the cells on the filter in the device the filter was viewed by microscopy. The results from the tumor cell suspension alone showed antibody-bead-tumor cell complexes clearly isolated on the filter. The results from the fluorescent labelled tumor cell suspension together with blood or bone marrow also showed antibody-bead-tumor cell complexes clearly isolated on the filter (FIG. 6). Additional experiments to test the sensitivity of the method showed that 100 tumor cells, when mixed with a suspension of $10^7$ blood or bone marrow cells, could be detected using this method.
4. Growth of separated cells isolated using the cell filter device. Tumor cell suspensions treated and isolated as described in the model experiments 1. and 2., were subjected to the filter device and the filter was subsequently incubated in a semi-solid medium containing 0.3% agarose in culture medium containing 20% calf serum. The cells were incubated in an atmosphere of 5% $CO_2$ at 37C. The tumor cells showed an ability to divide and grow.

In several experiments some unspecific binding to the mononuclear cells was observed, which was found to be unrelated to the nature of the specific antibody, and which was equally pronounced with SAM-coated particles alone. The magnitude of this unspecific binding varied from almost 0% to a level between 0.5–2%. This unspecific binding was almost eliminated by mild treatment with detergent, (TWEEN 20™ polyoxyethylenesorbitan monolaurate) performed to reduce the problem of hydrophobic cell interactions.

Examples of the Usefulness of the precedure

1. Detection of micrometastic neoplastic disease in blood and marrow. Early and reliable diagnosis of spread of cancer cells to blood and/or bone marrow has become increasingly important for the choice of optimal therapy, possibly curative in many types of cancer, including carcinomas, as described in application Example 1. Similar procedures for malignant melanoma, sarcoma, neuroblastoma and several other cancers have been established or are under development.
2. Detection of malignant cells in pleural or ascitic effusions and urine. The nature of such effusions may represent an important diagnostic problem, particularly when a low number of cancer cells are present together with normal reactive or epithelial cells. In several cases a definite diagnosis has been rapidly made with the new method, in cases where conventional cytological examination has been negative or inconclusive. A similar advantage can be found in cases of cancer in the kidneys or in the urinary tract and bladder.
3. Detection of neoplastic cells in the cerebrospinal fluid. As the systemic treatment of many cancer types have improved, the frequency of cases with symptom-giving brain metastases have significantly increased, and in parallell with this, the necessity for early detection of such spread. With the use of the new procedure even a low number of malignant cells can easily be identified, permitting intervention with therapeutic alternatives at an early stage of intracranial tumor manifestations.
4. Diagnosis of cancer in biopsied tissue. When cancer is suspected, and tissue biopsies are obtained by surgical procedures or by e.g. needle biopsies, a much more simple and rapid diagnosis can be made with the new method, used on prepared cell suspensions, compared to conventional morphological or immunohistochemical or cytochemical procedures. Distinction between several alternative cancers can be made by the use of the appropriate antibodies.
5. Identification of prognostic indicators. Since the expression of several membrane molecules have been shown to correlate with progression of the malignant disease in several cancers, the present method can be used to identify prognostic indicators, for example as described in application Example 2.
6. Identification of cells indicative of specific diseases or of disease progression or state. In various types of rheumatoid diseases (such as rheumatoid arthritis), as well as in allergic, autoimmune, and cardiovascular diseases, identification of the systemic or local presence of specific subpopulations of cells is important for diagnosis and for determining the stage of the disease. Rapid detection of such cell populations with the new method is therefore of considerable diagnostic and therapeutic importance.
7. Detection of subpopulations of normal cells. For several purposes, it will be important to detect the fraction of a particular subpopulation of normal cells in a population. This applies e.g. to liver biopsies where the identification of cells expressing the biliar epithelial antigen, may be of importance. Similarly, the identification, and possible isolation of specific endothelial cells from a cell suspension prepared from various normal tissues may be warranted.
8. Isolation and growth of selected cells. For many of the above mentioned purposes it may be required to have a larger population of cells to study. The present method using the cell filter device can provide the conditions to permit the propagation of the positively selected target cells, without the presence of free unbound particles or other unspecifically bound cells.

Several of the cell membrane molecules mentioned above in sections 1–6 may also be used as targets for immunotherapy with several types of activated killer cells or for example with immunotoxins. The identification with the new method of expression of such molecules is, therefore, also of value for determining in which cases such types of therapy should be used.

Examples of A Practical Application of the Method

Example 1

To diagnose spread of cancer cells in blood and/or bone marrow at an early stage, we have used in the new procedure the MOC-31, NrLu10, BM2, BM7, 12H12, and MLuCl anti-carcinoma antibodies to determine whether or not micrometastatic disease from breast, lung, colorectal, and prostate cancer might be sensitively identified in such body fluids. The successful results with these antibodies have significant clinical implications.

Example 2

The expression of many cell membrane molecules have been shown to correlate with progression of the malignant disease in several types of cancer. The detection of binding of such molecules to respective antibodies can therefore be used to obtain information of high prognostic value. Among such antigens are a high number of adhesion molecules, carbohydrate antigens, glycolipids, growth factor receptors and carcinoma markers listed below. We have, with the new procedure identified the binding of particle-antibody complexes to CD44 variants, E-cadherin, Le$^Y$, CEA, EGF-r. transferrin receptor, MUC-1 epitope, LUBCRU-G7 epitope, prostate cancer antigen, UJ13A epitope, 2-microglobulin, HLA-antigens, and apoptosis receptor.

Example 3

Two litres of pleural effusion from a patient supposed to suffer from malignant melanoma was obtained. After centrifugation, the cells were suspended in a volume of 2 ml of RPMI with a 10% fetal calf serum, incubated with 9.2.27 anti-melanoma antibody (10 g/ml) at 4C. for 30 min, washed and again incubated with Dynabeads™ SAM M450/IgG2A at 4C. for 30 min. The cell suspension was then examined under a microscope for determining the fraction of cells with paramagnetic cells attached to their surface. The diagnosis of malignant melanoma was confirmed, as about 10% of the cells had a significant number of bound particle-rosettes.

Example 4

Biopsied tissue was obtained from a subcutaneous tumor in a case with clinical indications of either small cell lung cancer or a malignant melanoma. A single cell suspension was prepared from the biopsy, divided in 2 fractions, one incubated with the 9.2.27 anti-melanoma antibody, and the other with MOC-31 anti-carcinoma antibody (both at 10 g/ml). The incubation was similar to that used in the example above. None of the cells incubated with the melanoma antibody bound any beads, whereas all tumor cells incubated with MOC-31 were positive.

Example 5

Biopsied tissue from a patient suspected to have malignant i5 melanoma was examined by preparing single cell suspension, incubating with 9.2.27 anti-melanoma antibody, and then following the procedure as above. Most of the cells were positive with a high number of particle-rosettes attached to their membranes Example 6

A pleural effusion from a breast cancer patient was studied to examine whether tumor cells could be detected in the fluid. One litre of the fluid was centrifuged, the cells resuspended, and in separate vials incubate with each of 3 different anticarcinoma antibodies (MOC-31, 2E11, 12H12). After completing the procedure as in the previous example, it was found that most of the cells bound to antibody-coated particles in all 3 cases.

Example 7

A bone marrow suspension obtained from a breast cancer patient was studied to examine whether micrometastic tumor cells could be present. After the preparation of mononuclear cells, these were incubated with the same 3 anti-carcinoma antibodies used in the example above, but in this case the antibodies were first attached to Dynabeads™ SAM IgG paramagneteic particles. After 1 incubation with these directly coated particles, the cell suspension was examined in the microscope, and a high number of cells were found positive with a number of particlerosettes attached to their membrane. Similar experiments have been performed in a number of pleural or ascitic effusion and bone marrow from patients with breast.

Example 8

T47D human breast carcinoma cells were incubated for varying lenghts of time with Hoechst fluoresence dye, -and the viability of the labeled cells was checked. Varying numbers of labeled breast carcinoma cells were then added to $1 \times 10^6$ bone marrow cells obtained from healthy volunteers. In different experiments, different concentrations of paramagnetic, monodisperse particles (Dynabeads™ P450) coated with individual anticarcinoma antibodies (NrLulO, MOC31, or 12H12) were added. After incubation for 30 min on ice, samples of the different test tubes were examined in a counting chamber under light and fluorescence microscopy. When the ratio of tumor cells/total nucleated cells was low, the cell suspension was subjected to a magnetic field and the cells with particles attached were isolated before examined in the microscope. It was found that at an optimal ratio of 1–10 paramagnetic beads per tumor cell in the cell mixture, all the tumor cells had from 2–15 beads attached to their surface. The sensitivity of the detection method was close to one target-cell per $10^4$ nucleated cells. In control experiments with labeled tumor cells using antibodies known to have some cross-reativity to normal cells, this cross-reactivity was confirmed with the antibody-coated paramagnetic particles. In experiments with beads without tumor-associated antibody coating, none of the target cells bound any beads.

Similar experiments have been performed both with other breast cancer lines and a small cell lung cancer cell line. Similar sensitivity and specificity were obtained in these experiments.

Example 9

Pleural and ascites fluid from patients with breast cancer and ovarian carcinoma were centrifuged, the same coated paramagnetic particles used in Example 1 were added, incubated and concentrated in a magnetic field before the suspension was examined under light microscopy. Typically, cells that had the clear morphological features of tumor cells had beads attached, whereas none of the few normal cells bound the antibody-coated beads. In two cases with pleural effusion, an independent morphological examination did not reveal the presence of any tumor cells, whereas a significant number malignant cells were detected by the use of antibody-coated beads. In some cases, tumor cells were separated in a magnetic field and transferred to tissue culture flasks containing growth medium specially prepared for growing breast cancer cells, in attempts to establish permanent cell lines from these cultures. In parallel, cells from the malignant effuisions were cultivated directly without positive selection with magnetic beads. In the latter cases, no cell line could be established, whereas in more than 50% of the cases where positively selected tumor cells had been used, cell lines were successfully established.

Example 10

In some cases, bone marrow and peripheral blood obtained from patients with breast cancer were examined with the present procedure by adding antibody-coated paramagnetic beads, incubating for 30 min at 4C. and concentrating in a magnetic field and by examining the suspension under light microscopy. In both cases binding of the paramagnetic beads to tumor cells, representing 0.1–1% of the nucleated cells in the bone marrow and blood was detected, cells that could not be identified by any other method.

Example 11

Antibodies against certain growth factor receptors or other gene products expressed on the surface of specific cell populations may be used to identify and positively select these cells. Beads coated with anti-transferrin receptor antibodies, used in the novel method according to the present invention were shown to represent a rapid, simple and sensitive method for identification of cells expressing the transferrin receptor.

Example 12

For various purposes isolation of specific populations of normal cells is warranted. Endothelial cells lining the capillary or small vessels in normal or tumorous tissue could be positively selected from cell suspensions prepared from the relevant tissues. The procedure involved the use of beads coated with antibody directed against structures expressed on the endothelial cells, but not on the other normal cells in the cell mixture.

Example 13

Human cells injected into immunodeficient rodents was shown to be present in cell suspensions prepared from tumor xenografts and from various host organs/tissues by employing magnetic particles coated with an anti-pan human antibody.

Example 14

Tumor cell lines from breast carcinoma and melanoma patients were separated from a mixed population of blood or bone marrow cells and filtered using the cell filter device described. After the addition of culture medium and subsequent incubation the selected tumor cells on the filter were able to grow in the absence of free unbound particles or other unspecifically bound cells.

TABLE 1

List of relevant antigens and examples of associated antigen-binding antibodies

| ANTIGENS | MONOCLONAL ANTIBODIES |
|---|---|
| Adhesion molecules | |
| Fibronectin receptor (=5β1 integrin) | Pierce 36114, BTC21/22 |
| | Calbiochem 341649 |
| Integrin α3β1 | M-Kiol 2 |
| Vitronectin receptor (αvβ3 integrin) | TP36.1, BTC 41/42 |
| Integrin α2 | Calbiochem 407277 |
| Integrin α3 | Calbiochem 407278 |
| Integrin α4 | Calbiochem 407279 |
| Integrin α5 | Calbiochem 407280 |
| Integrin αV | Calbiochem 407281 |
| Integrin β2 | Calbiochem 407283 |
| Integrin β4 | Calbiochem 407284 |
| GpIIβIIIa | 8221 |
| ICAM-I (CD54) | C57–60, CL203.4, RR 1/1[1] |
| VCAM-1 | Genzyme 2137-01 |
| ELAM-1 | Genzyme 2138-01 |
| E-selectin | BBA 8 |
| P-selectin/GMP-140 | BTC 71/72 |
| LFA-3 (CD58) | TS 2/9 |
| CD44 | BM 1441 272, 25:32 |
| CD44-variants | 11.24, 11.31, 11.10 |
| N-CAM (CD56) | MOC-1 |
| H-CAM | BCA9 |
| L-CAM | BM 1441 892 |
| N-CAM | TURA-27 |
| MACAM-1 | NKI-M9 |
| E-cadherin | BTC 111, HECD-1, 6F9 |
| P-cadherin | NCC-CAD-299 |
| Tenascin | BM 1452 193 |
| | Calbiochem 580664 |
| Thrombospondin receptor (CD36) | BM 1441 264 |
| VLA-2 | A1.43 |
| Laminin receptor | |
| HNK-1 epitope | HNK-1 |
| Carbohydrate antigens | |
| T-antigen | HH8, HT-8 |
| Tn-antigen | TKH6, BaGs2 |
| Sialyl Tn | TKH-2 |
| Gastrointestinal cancer associated antigen ($M_w$200kD) | CA 19-9 |
| Carcinoma associated antigen | C-50 |
| Le$^y$ | MLuC1, BR96, BR64 |
| di-Le$^x$, tri-Le$^x$ | B3 |
| Dimetric Le$^a$ epitope | NCC-ST-421 |
| H-type 2 | B1 |
| CA15-3 epitope | CA15-3 |
| CEA | I-9, I-14, I-27, II-10, I-46 |
| | Calbiochem 250729 |
| Galbl-4GlcNac (nL4,6,8) | 1B2 |
| H-II | BE2 |
| A type 3 | HH8 |
| Lacto-N-fucopentanose III (CD15) | PM-81 |
| Glycolipids | |
| GD$_3$ | ME36.1, R24 |
| GD$_2$ | ME36.1, 3F8, 14.18 |
| Gb$_3$ | 38-13 |
| GM$_3$ | M2590 |
| GM$_2$ | MKI-8, MKI-16 |
| FucGM$_1$ | 1D7, F12 |
| Growth factor receptors | |
| EGF receptor | 425.3.2.E9, 225 |
| c-erbB-2 (HER2) | BM 1378 988, 800 E6 |
| PDGFα receptor | Genzyme 1264-00 |
| PDGFβ receptor | Sigma P 7679 |
| Transferrin receptor | OKT 9, D65.30 |
| NGF receptor | BM 1198 637 |
| IL-2 receptor (CD25) | BM 1295 802, BM 1361 937 |
| c-kit | BM 428 616, 14 A3, 1D9.3D6 |
| TNF-receptor | Genzyme 1995-01, PAL-M1 |

TABLE 1-continued

List of relevant antigens and examples of associated antigen-binding antibodies

| ANTIGENS | MONOCLONAL ANTIBODIES |
|---|---|
| NGF-receptor | |
| Melanoma antigens | |
| High molelcular weight antigen (HMW 250.000) | 9.2.27, NrML5, 225.28 763.74,. TP41,2, IND1 |
| Mw105 melanoma-associated glycoprotein | ME20 |
| 100kDa antigen (melanoma/carcinoma) | 376.96 |
| gp 113 | MUC 18 |
| p95–100 | PAL-M2 |
| Sp75 | 15.75 |
| gr 100–107 | NKI-bereb |
| MAA | K9.2 |
| $M_r$125kD (gp125) | Mab 436 |
| Sarcoma antigens | |
| TP-1 and TP-3 epitope | TP-1, TP-3 |
| $M_w$200kD | 29–13, 29.2 |
| $M_w$160kD | 35–16, 30–40 |
| Carcinoma markers | |
| MOC-31 epitope (cluster 2 epithelial antigen) | MOC-31, NrLu10 |
| MUC-1 antigens (such as DF3-epitope (gp290kD) | MUC-1, DF3.BCP-7 to -10 |
| MUC-2 and MUC-3 | PMH1 |
| LUBCRU-G7 epitope (gp 230kD) | LUBCRU-G7 |
| Prostate specific antigen | BM1276 972 |
| Prostate cancer antigen | E4-SF |
| Prostate high molecular antigen $M_w$ > 400kD | PD41 |
| Polymorphic epithelial mucins | BM-2, BM-7, 12-H-12 |
| Prostate specific membrane antigen (Cyt-356) | 7E11-C5 |
| Human milk fat globulin | Immunotech HMFG-1, 27.1 |
| 42kD breast carcinoma epitope | B/9189 |
| $M_{w > 10}{}^6$ mucin | TAG-72, CC-49, CC-83 |
| Ovarian carcinoma OC125 epitope ($M_w$750 kD) | OC125 |
| Pancreatic HMW glycoprotein | DU-PAN-2 |
| Colon antigen Co17-1A($M_w$37000) | 17-1A |
| G9-epitope (coloncarcinoma) | G9 |
| Human colonic sulfomucin | 91.9H |
| $M_r$300kD pancreas antigen | MUSE11 |
| GA 733.2 | GA733,KS1.4 |
| TAG 72 | B72.3, CC49, CC83 |
| Undefined | Oa11, SM1 |
| Pancreatic cancer-associated | MUSE 11 |
| Pancarcinoma | CC49 |
| Prostate adenocarcinoma-antigen | PD 41 |
| $M_w$150–130kD adenocarcinoma of the lung | AF-10 |
| gp 160 lung cancer antigen (Cancer Res. 48, 2768, 1988) | anti gp160 |
| $M_w$92kD bladder carcinoma antigen | 3G2-C6 |
| $M_w$600kD bladder carcinoma antigen | C3 |
| Bladder carcinoma antigen (Cancer Res. 49, 6720, 1989) | AN43, BB369 |
| CAR-3 epitope $M_w$ > 400kD | AR-3 |
| MAM-6 epitope (C15.3) | 115D8 |
| High molecular ovarian cancer antigen | OVX1, OVX2 |
| Mucin epitope Ia3 | Ia3 |
| Hepatocellular carcinoma antigen $M_w$900kD | KM-2 |
| Hepemal epitope (gp43) Hepatocellular carc. ag | Hepema-1 |
| O-linked mucin containing N-glycolylneuraminic acid | 3E1.2 |
| $M_w$48kD colorectal carcinoma antigen | D612 |
| $M_w$71kD breast carcinoma antigen | BCA 227 |
| 16.88 epitope (colorectal carcinoma-antigen) | 16.88 |
| CAK1 (ovarian cancers) | K1 |
| Colon specific antigen p | Mu-1, Mu-2 |
| Lung carcinoma antigen $M_w$350–420kD | DF-L1, DF-L2 |
| gp54 bladder carcinoma antigen | T16 |
| gp85 bladder carcinoma antigen | T43 |
| gp25 bladder carcinoma antigen | T138 |
| Neuroblastorna antigens | |
| Neuroblastoma-associated, such as UJ13A epitope | UJ13A |
| Glioma antigens | |
| Mel-14 epitope | Mel-14 |
| Head and neck cancer antigens | |
| $M_w$18–22kD antigen | E48 |
| HLA-antigens | |
| HLA Class 1 | TP25.99 |
| HLA-A | VF19LL67 |
| HLA-B | H2-149.1 |
| HLA-A2 | KS1 |
| HLA-ABC | W6.32 |
| HLA-DR, DQ, DP | Q 5/13, B 8.11.2 |
| β2-microglobulin | NAMB-1 |
| Apoptosis receptor | |
| Apo-1 epitope | Apo 1 |
| Various | |
| Plasminogen activator antigens and receptors | Rabbit polylonal |
| p-glycoprotein | C219, MRK16.JSB-1, 265/F4 |
| cathepsin D | CIS-Diagnostici, Italy |
| biliary epithelial antigen | HEA 125 |
| neuroglandular antigen (CD63) | ME491, NKI-C3, LS62 |
| CD9 | TAPA-1, R2, SM23 |
| pan-human cell antigen | pan-H |

TABLE 2a

Results of antibody binding with different cell lines

| Antibodies | | Cell Line MCF-7 | Cell line SKBR3 | Cell line T47D | Cell line MDA231 | Cell line MDA435 | Cell line DU145 | Cell line FEMX-1 | Cell line LOX |
|---|---|---|---|---|---|---|---|---|---|
| NrLu10 | IgG2b | | + | + | (+) | (+) | + | | |
| Moc31 | IgG1 | + | + | + | (+) | (+) | (+) | + | |
| Moc1 | IgG1 | | | (+) | (+) | + | | | |
| 12H12 | IgG1 | | + | + | | + | + | | |
| 2E11 | IgG3 | + | + | + | | + | + | | |
| 5A6 | IgG1 | | (+) | + | | | | | |
| 5F2 | IgM | | | (+) | | | | | |
| CC3 | IgG2a | − | − | − | | | | − | |
| CC1 | IgM | | | − | | | | (+) | |
| CU18 | IgG1 | − | − | − | | | | | |
| CU46 | IgG1 | (+) | − | − | | | | | |
| 7F11 | IgG1 | − | − | + | | | − | − | − |
| ID7 | IgG3 | | | (+) | | | | | |
| E4SF | IgG1 | | + | + | | | (−) | − | 50%+ |
| 425-3 | | | | + | | | | − | + |
| 9.2.27 | | | | | | | | + | + |
| MUC18 | | | − | | | | | − | − |
| 2g12 | IgG1 | | | | | | | + | |
| 4b7 | | | | | | | | + | |
| IgG1 | | + | | + | | | | + | |
| BCRU-G7 | IgM | | | | | | | | |

TABLE 2b

Results of antibody binding with different cell lines

| Antibodies | | Cell Line PM1 | Cell line MA-11 | Cell line CRL-1435 | Cell line CRL-1740 | Cell line H-146 | Cell line Colo-205 | Cell line 786-O | Cell line WIDr |
|---|---|---|---|---|---|---|---|---|---|
| NrLu10 | IgG2b | + | + | + | + | + | + | − | |
| Moc31 | IgG1 | + | + | + | + | + | + | + | + |
| Moc1 | IgG1 | | | | | + | − | | |
| 12H12 | IgG1 | + | + | (+) | | − | − | − | |
| 2E11 | IgG3 | (+) | + | − | + | − | − | − | |
| 5A6 | IgG1 | + | + | | | | | | |
| CC3 | IgG2a | | | | | − | | − | |
| CC1 | IgM | | | | | (+) | | − | |
| CU18 | IgG1 | | | | | − | | − | |
| CU46 | IgG1 | | | | | − | | − | |
| 7F11 | IgG1 | (+) | + | − | | − | − | | − |
| ID7 | IgG3 | | | | | − | − | | − |
| E4SF | IgG1 | + | + | + | + | − | − | | − |
| MUC18 | | − | | | | | | | |
| 2g12 | IgG1 | | | | | − | | − | |
| 4b7 | IgG1 | | | | | − | | − | |
| BM2 (=2F11) | | + | + | | | | | | |
| BM7 (=7F11) | | + | | | | | | | |
| GINTES | IgG | | | | | + | − | | − |
| 3C9 | IgM | | | | | − | | | − |
| HH8 | IgM | | | | | − | | | − |
| 5F4 | IgM | | | | | − | | | − |
| 3F1 | IgG1 | | | | | − | | | − |

What is claimed is:

1. A method for detecting a specific target cell in a cell suspension, the cell suspension comprising a mixed cell population, a fluid system containing a mixed cell population, or a homogenous cell population prepared from a solid tissue, without detection of normal and malignant hematopoietic cells, the method comprising:

a. coating paramagnetic particles with an antibody or antibody fragment reactive with an antigen membrane structure specifically expressed on the target cell and not on a non-target cell in the cell suspension;

b. contacting the coated paramagnetic particles with the cell suspension;

c. incubating and rotating the mixture of coated paramagnetic particles and cell suspension;

d. incubating the mixture of coated paramagnetic particles and cell suspension with an additional antibody or antibody fragment that is the same or different as that stated in (a), and binding the additional antibody or fragment to an antigen membrane structure specifically expressed on the target cell, that is the same or different as that stated in (a), and wherein the additional antibody or fragment is labeled;

e. separating particle-target cell complexes from unbound particles, unspecifically bound non-target cells and unbound non-target cells in the mixture of coated paramagnetic particles and cell suspension by transferring the mixture to a separating apparatus, the separating apparatus comprising a filter having a pore size and shape capable of retaining particle-target cell complexes or rosettes and which filter provides a matrix for cell growth;

f. growing cells of the separated particle-target cell complexes on the filter; and g. detecting labeled antibody/target cell/particle-immobilized antibody, labeled target cell/particle-immobilized antibody, or labeled antibody/target cell complexes and counting the complexes.

2. The method of claim 1, wherein the paramagnetic particle is coated with a murine or a human antibody or a fragment thereof.

3. The method of claim 1, wherein the incubating and rotating of the mixture, or the incubating of the mixture with the additional antibody or antibody fragment, or both, last for 5–10 minutes to 2 hours.

4. The method of claim 3, wherein the incubating and rotating of the mixture, or the incubating of the mixture with the additional antibody or antibody fragment, or both, last 30 minutes.

5. The method of claim 1, wherein the incubating and rotating of the mixture, or the incubating of the mixture with the additional antibody or antibody fragment, or both, are at a temperature between 0° C. and 25° C.

6. The method of claim 5, wherein the incubating and rotating of the mixture, or the incubating of the mixture with the additional antibody or antibody fragment, or both, are at a temperature of 4° C.

7. The method of claim 1, further comprising pre-incubating the antibody-coated paramagnetic particle, or the cell suspension, or both, with a detergent capable of eliminating hydrophobic cell interactions prior to incubating and rotating the mixture, wherein the detergent comprises polyoxyethylenesorbitan monolaurate at a concentration less than 0.1% and the preincubation lasts 30 minutes at 4° C.

8. The method of claim 1, further comprising:
subjecting the incubated mixture of coated paramagnetic particles and cell suspension to a magnetic field to separate any of said particle-target cell complexes from the incubated mixture.

9. The method of claim 8, further comprising:
immunohistochemical chromogenic staining of the labeled antibody/target cell/particle-immobilized antibody, labeled target cell/particle-immobilized antibody or labeled antibody/target cell complexes.

10. The method of claim 1, wherein the step of detecting comprises visualizing labeled antibody/target cell/particle-immobilized antibody, labeled target cell/particle-immobilized antibody, or labeled antibody/target cell complexes in the cell suspension employing a microscope, or counting labeled antibody/target cell/particle-immobilized antibody, labeled target cell/particle-immobilized antibody, or labeled antibody/target cell complexes in the cell suspension employing a cell or particle counting device.

11. The method of claim 1, further comprising:
fixing the cell suspension by pretreating the cell suspension with a fixative selected from the group consisting of formalin and alcohol.

12. The method of claim 2, wherein the additional antibody or fragment is labeled with an enzyme; the detection step comprises contacting the particle-target cell complexes with a chromogenic substrate which reacts with the enzyme to produce a visible product.

13. The method of claim 12, wherein the enzyme is peroxidase or alkaline phosphatase.

14. The method of claim 12, wherein the additional antibody or fragment is biotinylated, the enzyme is complexed to avidin, and labeling comprises forming a complex between the biotinylated antibody or fragment and the avidin complexed enzyme.

15. The method of claim 1, wherein the label is a non-paramagnetic particle that can be visualized directly because of color or complexation of the particle-target cell with a chromogenic substrate which reacts with the enzyme to produce a visible product.

16. The method of claim 1, wherein the separating apparatus further comprises a filtrate collection box, a lid, a plurality of multiwell units, and a filter support, and wherein the filter and filter support are detachably fixed to the bottom of the multiwell unit.

17. The method of claim 16, further comprising the step of: fixing the filter and retained target cell.

18. The method of claim 16, further comprising contacting the removed filter with a culture medium to establish in vitro cell cultures from the retained complexes.

19. The method of claim 16, further comprising examining the target cells by biological, biochemical or immunological examination procedures for identifying the presence of one or more specific DNA, mRNA or protein in the target cells.

20. The method of claim 19, wherein the biological or biochemical examination comprises polymerase chain reaction (PCR) and reverse transcriptase PCR.

21. The method of claim 16, wherein the filter is fabricated from a material containing pores having a regular and consistent shape and size.

22. The method of claim 21, wherein the size and shape of the pores is sufficient to retain particle-target cell complexes, while allowing unbound particles, unspecifically bound non-target cells, and unbound non-target cells to pass through the filter.

23. The method of claim 21, wherein the material comprises a nylon monofilament membrane.

24. The method of claim 21, wherein the pores have a size of 20 μm.

25. The method of claim 16, wherein the separating apparatus further comprises a material that is capable of culturing tissues.

26. The method of claim 1, wherein the antibody or fragment thereof is reactive with an antigen of a normal, living target cell.

27. The method of claim 26, wherein the target cell is a liver hepatocyte, a Kupffer cell, an endothelial cell type 1 or 2, a Clara cell of the lung, a pancreatic exocrine cell, a kidney tubule cell, a bladder epithelial cell, a brain glial or ependymal cell, a prostate epithelial cell, a ciliated cell of an airway, a mucosal cell in a gastrointestinal tract, a pituitary cell, or an endocrine cell in a hormone producing organ.

28. The method of claim 1, wherein the antibody or fragment thereof is reactive with a growth factor receptor on a membrane of a normal cell.

29. The method of claim 28, wherein the growth factor receptor is an epidermal growth factor (EGF)_-receptor, a platelet derived growth factor (PDGF) A receptor, a PDGF B receptor, an insulin receptor, an insulin-like growth factor receptor, a transferrin receptor, a nerve growth factor (NGF)_receptor, or a fibroblast growth factor (FGF) receptor.

30. The method of claim 1, wherein the antibody or fragment thereof is reactive with an adhesion membrane molecule or a multiple drug resistance (MDR) protein of a normal cell.

31. The method of claim 1, wherein the target cell is a cell with abnormal developmental patterns and the antibody or fragment thereof is reactive with an antigen or a receptor on the cell with abnormal developmental patterns.

32. The method of claim 31, wherein the cell with abnormal developmental patterns is a primary and metastatic cancer cell.

33. The method of claim 31, wherein the antibody or antibody fragment is reactive with breast, ovarian or lung carcinoma cells; melanoma, sarcoma, glioblastoma or cancer cells of a gastrointestinal tract; melanoma, sarcoma, glioblastoma or cancer cells of a genitourinary tract; or melanoma, sarcoma, glioblastoma or cancer cells of a reticuloendothelial system.

34. The method of claim 31, wherein the antibody or antibody fragment is reactive with cells of a non-neoplastic disease.

35. The method of claim 34, wherein the non-neoplastic disease is of a cell selected from the group consisting of a cardiovascular cell, a neurological cell, a pulmonary cell, an autoimmune cell, a gastrointestinal cell, a genitourinary cell, and a reticuloendothelial cell.

36. The method of claim 1, wherein the antibody or fragment thereof is an IgG isotype, a $F(ab')_2$ fragment, a $F(ab)$ fragment, an IgM, or a fragment of IgM.

37. The method of claim 1, wherein the cell suspension comprises mammalian tissue, a pleural effusion, a peritoneal effusion, a bodily fluid, or a solid tumor in a normal tissue or organ.

38. The method of claim 37, wherein the mammalian tissue is selected from the group consisting of human bone marrow and human peripheral blood; the bodily fluid is selected from the group consisting of urine, cerebrospinal fluid, semen, and lymph; and the normal tissue or organ is selected from the group consisting of liver, lymph node, spleen, lung, pancreas, bone, central nervous system, prostate gland, skin, and mucous membranes.

39. The method of claim 1, wherein the antibody or antibody fragment, the additional antibody or antibody fragment, or both is reactive with fibronectin receptor, β-integrin, vitronectin receptor, αγβ33-integrin, P-selectin, GMP-140, CD44-variants, N-CAM, E-cadherin, $Le^Y$, CEA carcinoembryonic antigen, EGF embryonic growth factor receptor, c-erbB-2, HER2, transferin receptor, TNF tumor necrosis factor-receptor, high molecular weight melanoma antigen Mw 250 kDa, p95–100, TP-1 and TP-3 epitope, sarcoma antigen Mw 200 kDa, sarcoma antigen Mw 160 kDa, MOC-31 epitope, cluster 2 epithelial antigen, MUC-1 antigen, DF3-epitope, gp290 kDa, prostate high molecular weight antigen Mw>400 kDa, TAG 72, bladder carcinoma antigen Mw 48 kDa colorectal carcinoma antigen, lung carcinoma antigen Mw 350–420 kDa, Mel-14 epitope, $β_2$-microglobulin, Apo-1 epitope, or pan-human cell antigen.

40. A kit for performing a method for detecting a specific target cell in a cell suspension, the cell suspension comprising a mixed cell population, a fluid system containing a mixed cell population, or a homogenous cell population prepared from a solid tissue, without detection of normal and malignant hematopoietic cells, the kit comprising:
   a. a first antibody or antibody fragment that is capable of reacting with an antigen on said target cell, and wherein the antibody or fragment thereof is coated into a paramagnetic particle;
   b. the paramagnetic particle;
   c. a second antibody or antibody fragment, that is the same or different as that stated in (a), reactive with an antigen that is the same or different as that stated in (a) or a receptor on the target cell; wherein the antibody or antibody fragment is bound to biotin, avidin, an enzyme, a colored non-paramagnetic particle, a non-paramagnetic particle with a bound enzyme, or a combination thereof;
   d. an apparatus for separating particle-target cell complexes from unbound particles, unspecifically bound non-target cells and unbound non-target cells in the mixture of paramagnetic particles and cell suspension, the apparatus comprising a filtrate collection box, a lid, a plurality of multiwell units, a cell separator membrane filter having a pore size and shape capable of retaining particle-target cell complexes or rosettes and which filter provides a matrix for cell growth, and a filter support; wherein the filter and filter support are detachably fixed to the bottom of the multiwell unit; and
   e. a paramagnetic or non-paramagnetic particle precoated with a specific target cell antigen for use as a control or standard; wherein the antigens can be the same or different.

41. The kit of claim 40, wherein the enzyme is peroxidase or alkaline phosphatase.

42. The kit of claim 40, wherein the filter is fabricated from a material containing pores, the pores having a size of 20 μm.

43. A method for detecting a specific target cell in a cell suspension, the cell suspension comprising a mixed cell population, a fluid system containing a mixed cell population, or a homogenous cell population prepared from a solid tissue, without detection of normal and malignant hematopoietic cells, the method comprising:
   a. pre-coating paramagnetic particles with an antibody reactive with an Fc-portion of an antibody or an antibody fragment reactive with a membrane structure specifically expressed on the target cell and not on a non-target cell in the cell mixture;
   b. incubating the cell suspension with an additional antibody or antibody fragment that binds to an extracellular or intracellular molecule present in the target cell, wherein the additional antibody or fragment is labeled;
   c. contacting the precoated paramagnetic particles with the cell suspension to form a complex comprising the pre-coated paramagnetic particles, the antibody or antibody fragment reactive with a membrane structure specifically expressed on the target cell and not on a non-target cell in the cell mixture, and the target cell;
   d. separating particle/antibody/target cell/additional antibody or antibody fragment complexes from unbound particles, unspecifically bound non-target cells and unbound non-target cells in the mixture of coated paramagnetic particles and cell suspension by transferring the mixture to a separating apparatus, the separating apparatus comprising a filter having a pore size and shape capable of retaining particle-target cell complexes or rosettes and which filter provides a matrix for cell growth;
   e. growing cells of the separated particle-target cell complexes on the filter; and
   f. counting the particle/antibody/target cell/additional antibody or antibody fragment complexes.

44. The method of claim 43, wherein the step of forming the complex comprises:
   coating the pre-coated paramagnetic particles with an antibody or antibody fragment reactive with the membrane structure specifically expressed on the target cell and not on a non-target cell in the cell suspension;

contacting the coated, precoated paramagnetic particles with the cell suspension containing target cells; and incubating the mixture of coated paramagnetic particles and cell suspension under rotation.

45. The method of claim 44, wherein incubating the mixture of coated paramagnetic particles and cell suspension lasts for 5–10 minutes to 2 hours.

46. The method of claim 44, wherein incubating the mixture of coated paramagnetic particles and cell suspension lasts 30 minutes.

47. The method of claim 44, wherein incubating the mixture of coated paramagnetic particles and cell suspension is conducted at a temperature between 0° C. and 25° C.

48. The method of claim 44, wherein incubating the mixture of coated paramagnetic particles and cell suspension is conducted at a temperature of about 4° C.

49. The method of claim 43, wherein the step of forming the complex comprises:

mixing additional antibodies reactive with the membrane structure specifically expressed on the target cell and not on a non-target cell in the cell mixture with the cell suspension containing the target cells;

incubating the mixture under rotation;

adding the pre-coated paramagnetic particles to the incubating mixture; and continuing the incubation.

50. The method of claim 49, wherein incubating the mixture lasts for 5–10 minutes to 2 hours.

51. The method of claim 49, wherein incubating the mixture lasts 30 minutes.

52. The method of claim 49, wherein incubating the mixture is conducted at a temperature between 0° C. and 25° C.

53. The method of claim 49, wherein incubating the mixture is conducted at a temperature of about 4° C.

54. The method of claim 43, wherein the antibody or antibody fragment reactive with the membrane structure specifically expressed on the target cell and not on a non-target cell in the cell mixture is a murine or a human antibody or fragment thereof.

55. The method of claim 43, further comprising preincubating the antibody-coated paramagnetic particle, or the cell suspension, or both, with a detergent capable of eliminating hydrophobic cell interactions prior to incubating the cell suspension, wherein the detergent comprises polyoxyethylenesorbitan monolaurate at a concentration less than 0.1% and the preincubation lasts 30 minutes at 4° C.

56. The method of claim 43, the method further comprising:

subjecting the complex to a magnetic field to separate any of said particle-target cell complexes from the mixture of coated paramagnetic particles and cell suspension.

57. The method of claim 56, fuirther comprising:

immunohistochemical chromogenic staining of the labeled antibody/target cell/particle-immobilized antibody, labeled target cell/particle-immobilized antibody or labeled antibody/target cell complexes.

58. The method of claim 43, wherein the step of counting comprises visualizing and counting labeled antibody/target cell/particle-immobilized antibody, labeled target cell/particle-immobilized antibody, or labeled antibody/target cell complexes in the cell suspension employing a microscope or a cell or particle counting device.

59. The method of claim 43, further comprising the steps of:

isolating the target_cells by exposing the complex of cells and paramagnetic particles to a magnetic field to magnetically aggregate the cells;

subjecting the magnetically aggregated cells to further biological, biochemical, and immunological examination.

60. The method of claim 43, fuirther comprising:

fixing the cell suspension by pretreating the cell suspension with a fixative selected from the group consisting of formalin and alcohol.

61. The method of claim 43, wherein the label comprises an enzyme, the detection step comprises contacting the particle-target cell complexes with a chromogenic substrate which reacts with the enzyme to produce a visible product, and the counting step comprises measuring the amount of said visible product produced.

62. The method of claim 61, wherein the enzyme is peroxidase or alkaline phosphatase.

63. The method of claim 61, wherein the labeled antibody or fragment is biotinylated, the enzyme is complexed to avidin, and labeling comprises forming a complex between the biotinylated antibody or fragment and the avidin complexed enzyme.

64. The method of claim 43, wherein the label is a non-paramagnetic particle that can be visualized directly because of color or complexation of the particle-target cell with a chromogenic substrate which reacts with an enzyme to produce a visible product.

65. The method of claim 43, wherein the separating apparatus further comprises a filtrate collection box, a lid, a plurality of multiwell units, and a filter support; wherein the filter and the filter support are detachably fixed to the bottom of the multiwell unit.

66. The method of claim 65, further comprising the step of:

fixing the filter and retained target cell.

67. The method of claim 65, further comprising contacting the removed filter with a culture medium to establish in vitro cell cultures from the retained complexes.

68. The method of claim 65, further comprising examining the target cells by biological, biochemical or immunological examination procedures for identifying the presence of one or more specific DNA, mRNA or protein in the target cells.

69. The method of claim 68, wherein the biological or biochemical examination comprises polymerase chain reaction (PCR) and reverse transcriptase PCR.

70. The method of claim 43, wherein the antibody or fragment thereof is reactive with an antigen of a normal, living target cell.

71. The method of claim 70, wherein the target cell is a liver hepatocyte, a Kupffer cell, an endothelial cell type 1 or 2, a Clara cell of the lung, a pancreatic exocrine cell, a kidney tubule cell, a bladder epithelial cell, a brain glial or ependymal cell, a prostate epithelial cell, a ciliated cell of an airway, a mucosal cell in a gastrointestinal tract, a pituitary cell, or another endocrine cell in a hormone producing organ.

72. The method of claim 43, wherein the antibody or fragment thereof is reactive with an antigen present on a subpopulation of normal cells and with oncogenic products expressed on the membrane of normal tissue cells.

73. The method of claim 43, wherein the antibody or fragment thereof is reactive with a growth factor receptor on a membrane of a normal cell.

74. The method of claim 23, wherein the growth factor receptor is an epidermal growth factor (EGF)_-receptor, a platelet derived growth factor (PDGF) A receptor, a PDGF B receptor, an insulin receptor, an insulin-like growth factor receptor, a transferrin receptor, a nerve growth factor (NGF)_ receptor, or a fibroblast growth factor (FGF) receptor.

75. The method of claim 43, wherein the target cell ant body or fragment thereof is reactive with an adhesion membrane molecule or a multiple drug resistance (MDR) protein of a normal cell.

76. The method of claim 43, wherein the target cell is a cell with abnormal developmental patterns and the antibody or fragment thereof is reactive with an antigen or a receptor on said cell with abnormal developmental patterns.

77. The method of claim 76, wherein the cell with abnormal developmental patterns is a primary and metastatic cancer cell.

78. The method of claim 76, wherein the antibody or antibody fragment is reactive with breast, ovarian or lung carcinoma cells; melanoma, sarcoma, glioblastoma or cancer cells of a gastrointestinal tract; melanoma, sarcoma, glioblastoma or cancer cells of a genitourinary tract; or melanoma, sarcoma, glioblastoma or cancer cells of a reticuloendothelial system.

79. The method of claim 76, wherein the antibody or antibody fragment is reactive with cells of a non-neoplastic disease.

80. The method of claim 79, wherein the non-neoplastic disease is of a cell selected from the group consisting of a cardiovascular cell, a neurological cell, a pulmonary cell, an autoinmnune cell, a gastrointestinal cell, a genitourinary cell, and a reticuloendothelial cell.

81. The method of claim 43, wherein the target cell antibody or fragment thereof is an IgG isotype, a F(ab')$_2$ fragment, a F(ab) fragment, an IgM, or a fragment of IgM.

82. The method of claim 43, wherein the cell suspension is selected from the group consisting of mammalian tissue, a pleural effusion, a peritoneal effusion, a bodily fluid, and a solid tumor in a normal tissue or organ.

83. The method of claim 82, wherein the mammalian tissue is selected from the group consisting of human bone marrow and human peripheral blood; the bodily fluid is selected from the group consisting of urine, cerebrospinal fluid, semen, and lymph; and the normal tissue or organ is selected from the group consisting of liver, lymph node, spleen, lung, pancreas, bone, central nervous system, prostate gland, skin, and mucous membranes.

84. The method of claim 43, wherein the antibody or antibody fragment, the additional antibody or antibody fragment, or both is reactive with fibronectin receptor, β-integrin, vitronectin receptor, αγβ3-integrin, P-selectin, GMP- 140, CD44-variants, N-CAM, E-cadherin, Le$^y$, CEA, EGF receptor, c-erbB-2, HER2, transferin receptor, TNF-receptor, high molecular weight meloanoma antigen Mw 250 kDa, p95–100, TP- 1 and TP-3 epitope, sarcoma antigen Mw 200 kDa, sarcoma antigen Mw 160 kDa, MOC-31 epitope, cluster 2 epithelial antigen, MUC- 1 antigen, DF3-epitope gp 290 KDa prostate high molecular weight antigen Mw>400 kDa, TAG 72, bladder carcinoma antigen, Mw 48 kDa colorectal carcinoma antigen, lung carcinoma antigen Mw 350–420 kDa, Mel-14 epitope, β$_2$-microglobulin, Apo-1 epitope, or pan-human cell antigen.

85. The method of claim 43, wherein the filter is fabricated from a material containing pores, the pores having a size of 20 μm.

86. A kit for performing a method for detecting a specific target cell in a cell suspension, the cell suspension comprising a mixed cell population, a fluid system containing a mixed cell population, or a homogenous cell population prepared from a solid tissue, without detection of normal and malignant hematopoietic cells, the kit comprising:

a. a first antibody or antibody fragment reactive with a membrane structure specifically expressed on the target cell and not on a non-target cell in the cell mixture;

b. a second antibody or antibody fragment reactive with an Fc-portion of the first antibody, wherein the second antibody or fragment thereof is coated onto a paramagnetic particle;

c. the paramagnetic particle; and d. a third antibody or antibody fragment, that is the same or different as that stated in (a), reactive with an antigen or membrane structure that is the same or different as that stated in (a) or a receptor within or on the target cell; wherein said antibody or antibody fragment is conjugated to biotin, an enzyme, or a non-paramagnetic particle with a specific color or with a bound enzyme;

e. an apparatus for separating particle-target cell complexes from unbound particles, unspecifically bound non-target cells and unbound non-target cells in a cell suspension of mixed cell populations, the apparatus comprising a filtrate collection box, a lid, a plurality of multiwell units, a cell separator membrane filter having a pore size and shape capable of retaining particle-target cell complexes or rosettes and which filter provides a matrix for cell growth, and a filter support; the filter and filter support are detachably fixed to the bottom of the multiwell unit; and f. a paramagnetic or non-paramagnetic particle precoated with a specific target cell antigen or group of antigens for use as a control or standard.

87. The kit of claim 86, wherein the enzyme is peroxidase or alkaline phosphatase.

88. The kit of claim 86, wherein the filter is fabricated from a material containing pores, the pores having a size of 20 μm.

* * * * *